(12) United States Patent
Harris et al.

(10) Patent No.: US 11,998,216 B2
(45) Date of Patent: Jun. 4, 2024

(54) SURGICAL CLIP APPLIER EMPLOYING ARCUATE SURGICAL CLIPS

(71) Applicant: Cilag GmbH International, Zug (CH)

(72) Inventors: Demetrius Harris, Cincinnati, OH (US); Joshua Young, Loveland, OH (US); Sarah Worthington, Maineville, OH (US); Stephen D. Geresy, West Chester, OH (US)

(73) Assignee: Cilag GmbH International, Zug (CH)

( * ) Notice: Subject to any disclaimer, the term of this patent is extended or adjusted under 35 U.S.C. 154(b) by 650 days.

(21) Appl. No.: 17/092,864

(22) Filed: Nov. 9, 2020

(65) Prior Publication Data

US 2021/0052276 A1 Feb. 25, 2021

Related U.S. Application Data

(62) Division of application No. 15/891,603, filed on Feb. 8, 2018, now Pat. No. 10,828,043.

(51) Int. Cl.
*A61B 17/12* (2006.01)
*A61B 17/122* (2006.01)
(Continued)

(52) U.S. Cl.
CPC ........ *A61B 17/1285* (2013.01); *A61B 17/122* (2013.01); *A61B 34/25* (2016.02);
(Continued)

(58) Field of Classification Search
CPC ..... A61B 17/122; A61B 17/10; A61B 17/068; A61B 17/128; A61B 17/1285;
(Continued)

(56) References Cited

U.S. PATENT DOCUMENTS 3,777,538 A * 12/1973 Weatherly .......... A61B 17/1285
606/142
4,296,751 A * 10/1981 Blake, III ............ A61B 17/128
606/143
(Continued)

FOREIGN PATENT DOCUMENTS

EP 2412318 A2 2/2012

*Primary Examiner* — Alexander J Orkin
(74) *Attorney, Agent, or Firm* — Vorys, Sater, Seymour and Pease LLP

(57) ABSTRACT

A method includes positioning a surgical tool with an end effector adjacent a surgical site, the end effector including a housing having a tapered section that defines an inner surface, first and second arcuate jaw members protruding distally from the housing and defining a channel therebetween, each arcuate jaw member exhibiting a curved profile shaped to receive an arcuate surgical clip, and a feedbar movable within the housing. The method further including urging the arcuate surgical clip against the inner surface, advancing the feedbar within the housing to engage and follow the inner surface and thereby flexing the feedbar downward and into engagement with the arcuate surgical clip, advancing the arcuate surgical clip with the feedbar into interposition between the first and second arcuate jaw members, and collapsing the first and second arcuate jaw members to crimp the arcuate surgical clip.

20 Claims, 13 Drawing Sheets

(51) Int. Cl.
  *A61B 17/128* (2006.01)
  *A61B 34/00* (2016.01)
  *A61B 34/37* (2016.01)
  *A61B 17/00* (2006.01)
  *A61B 17/10* (2006.01)
  *A61B 17/29* (2006.01)
  *A61B 34/30* (2016.01)

(52) U.S. Cl.
  CPC .............. *A61B 34/37* (2016.02); *A61B 34/71* (2016.02); *A61B 2017/00477* (2013.01); *A61B 17/10* (2013.01); *A61B 2017/2945* (2013.01); *A61B 2034/302* (2016.02); *A61B 2034/305* (2016.02); *A61B 34/70* (2016.02)

(58) Field of Classification Search
  CPC .. A61B 2017/2945; A61B 2017/00477; A61B 34/25; A61B 34/37; A61B 34/71; A61B 34/70; A61B 2034/302; A61B 2034/305; A61B 17/0682
  USPC ........................................................ 606/143
  See application file for complete search history.

(56) References Cited

U.S. PATENT DOCUMENTS

| | | | |
|---|---|---|---|
| 4,492,232 A | 1/1985 | Green et al. | |
| 5,292,326 A * | 3/1994 | Green | A61B 17/04 227/181.1 |
| 5,474,566 A * | 12/1995 | Alesi | A61B 17/1285 606/205 |
| 5,720,756 A | 2/1998 | Green et al. | |
| 5,833,696 A * | 11/1998 | Whitfield | A61B 17/1285 606/143 |
| 5,843,097 A * | 12/1998 | Mayenberger | A61B 17/1285 606/139 |
| 5,868,761 A | 2/1999 | Nicholas et al. | |
| 6,599,298 B1 * | 7/2003 | Forster | A61B 17/128 606/139 |
| 7,621,926 B2 | 11/2009 | Wixet et al. | |
| 8,403,945 B2 * | 3/2013 | Whitfield | A61B 17/105 606/143 |
| 8,403,946 B2 * | 3/2013 | Whitfield | A61B 17/1285 606/143 |
| 9,232,979 B2 | 1/2016 | Parihar et al. | |
| 9,358,015 B2 * | 6/2016 | Sorrentino | A61B 90/03 |
| 9,561,038 B2 * | 2/2017 | Shelton, IV | A61B 34/30 |
| 9,968,362 B2 * | 5/2018 | Malkowski | A61B 17/1285 |
| 2004/0193213 A1 * | 9/2004 | Aranyi | A61B 17/1285 606/205 |
| 2008/0243145 A1 * | 10/2008 | Whitfield | A61B 90/08 606/143 |
| 2009/0228024 A1 * | 9/2009 | Whitfield | A61B 17/1285 606/143 |
| 2011/0224696 A1 | 9/2011 | Huitema et al. | |
| 2014/0005695 A1 * | 1/2014 | Shelton, IV | A61B 34/30 606/143 |
| 2016/0287252 A1 | 10/2016 | Parihar | |

* cited by examiner

SURGICAL CLIP APPLIER EMPLOYING ARCUATE SURGICAL CLIPS

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which one or more small incisions are formed in the abdomen of a patient and a trocar is inserted through each incision to form a surgical access pathway for a surgical tool and elongate shaft. Once located within the abdomen, the surgical tool may engage and/or treat tissue in a number of ways to achieve a diagnostic or therapeutic effect. Manipulation and engagement of the surgical tool may take place via various components passing through the elongate shaft.

Robotic surgery represents a specialized class of laparoscopic surgical procedures. Instead of directly engaging a surgical tool, as in traditional laparoscopic surgery, a surgeon in a robotic surgical procedure instead manipulates and engages the surgical tool using an electronic interface communicatively coupled to a robotic manipulator. Manipulation and engagement of a surgical tool under robotic control can allow much more precise surgical procedures to be performed in many instances. To provide natural, hand-like articulation during a robotic surgical procedure, robotic surgical tools may incorporate an articulable "wrist" that couples an end effector to the elongate shaft. As used herein, the term "end effector" refers to the clinically active portion of a surgical tool. The wrist can also facilitate an expanded and more complex range of motion than is possible with a human wrist, which can allow highly elaborate and precise surgical procedures to be performed.

The end effectors of MIS tools are often similar in design to tools used in traditional surgical procedures, with the exception of the MIS I tools being sized to extend through a trocar and configured for actuation using one or more components extending through the elongate shaft. One type of MIS tool comprises a clip applier as an end effector, which can be used to ligate blood vessels, ducts, shunts, or portions of a bodily tissue during a surgical procedure. Clip appliers used in MIS procedures include a pair of movable opposed jaw members at a distal end of the elongate shaft for manipulating and crimping a surgical clip ("ligation clip") in between. In operation, a physician may position the opposed jaw members and an open surgical clip around a vessel, duct, or similar structure and actuate the surgical tool to bring the jaw members together, thereby collapsing the surgical clip to shut off fluid flow through the vessel or duct.

During the course of a MIS procedure, a surgeon may need to place multiple surgical clips in succession on one or more anatomical structures. Although MIS clip appliers may include a single surgical clip, it can be more desirable for multiple surgical clips to be housed in the clip applier to allow completion of a MIS procedure with a single insertion of the clip applier to a surgical site. Otherwise, a surgeon may have to utilize multiple clip appliers or withdraw the clip applier from a surgical site, load a new surgical clip into the end effector, and then reintroduce the clip applier to the surgical site. Both of these approaches may increase the time, complexity, cost and risk of a MIS procedure. Accordingly, clip appliers capable of housing multiple surgical clips can be desirable.

Wristed clip appliers presently available for MIS procedures have several significant limitations. The wrist architecture in conventional MIS tools generally precludes feeding finished surgical clips through the wrist to reach the opposed jaw members of the end effector. As a result, wristed clip appliers may incorporate one or more surgical clips distal to the wrist for feeding into the opposed jaw members. Because the space distal to the wrist is small, however, the number of surgical clips that may be housed in this location is rather limited. In some instances, the number of surgical clips housed distal to the wrist may be insufficient to complete a given surgical procedure. Conventional loading approaches may be similar to those described in U.S. Pat. No. 5,743,456, which is incorporated herein by reference in its entirety.

Moreover, increasing the size of the surgical tool distal to the wrist so that more surgical clips may be accommodated can be problematic in its own right. Specifically, a larger distal tool size increases the tool length undergoing articulation (i.e., a longer end effector), which can make accurate articulation more difficult. In addition, a larger tool size distal to the wrist may render the surgical tool incompatible with other components used in a surgical procedure. Visibility within a surgical site may also be problematic in some cases.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is directed to end effectors for surgical clip appliers and related surgical tools and, more particularly, to surgical clip appliers having improved clip loading capacity, particularly wristed surgical clip appliers.

As discussed above, supplying surgical clips to a wristed clip applier can be problematic, due both to the difficulty of feeding surgical clips through the wrist and housing a sufficient number of surgical clips within the surgical tool for eventual deployment during a surgical procedure. These issues are often not mutually exclusive of one another, since housing surgical clips distal to the wrist to address the feeding issue places the surgical clips in a location where a limited number of surgical clips may be housed. The present disclosure describes various approaches for promoting more efficient packing and dispensation of surgical clips distal to the wrist in a wristed clip applier without significantly increasing the size (length) of the distal portion of the surgical tool, specifically the end effector. The various tool configurations disclosed herein may afford other benefits as well, as will become apparent to one having ordinary skill in the art upon reading the present disclosure. Moreover, it is to be further appreciated that the clip packing and dispensation features of the present disclosure may likewise be incorporated in non-wristed surgical clip appliers and similar surgical tools while still affording at least some of the advantages described herein.

Before discussing additional details of the surgical clip appliers of the present disclosure and methods for their use, a brief overview of laparoscopic and similar surgical tools and robotic surgical systems will be provided hereinafter in order for the embodiments of the present disclosure to be better understood.

Figure 1:
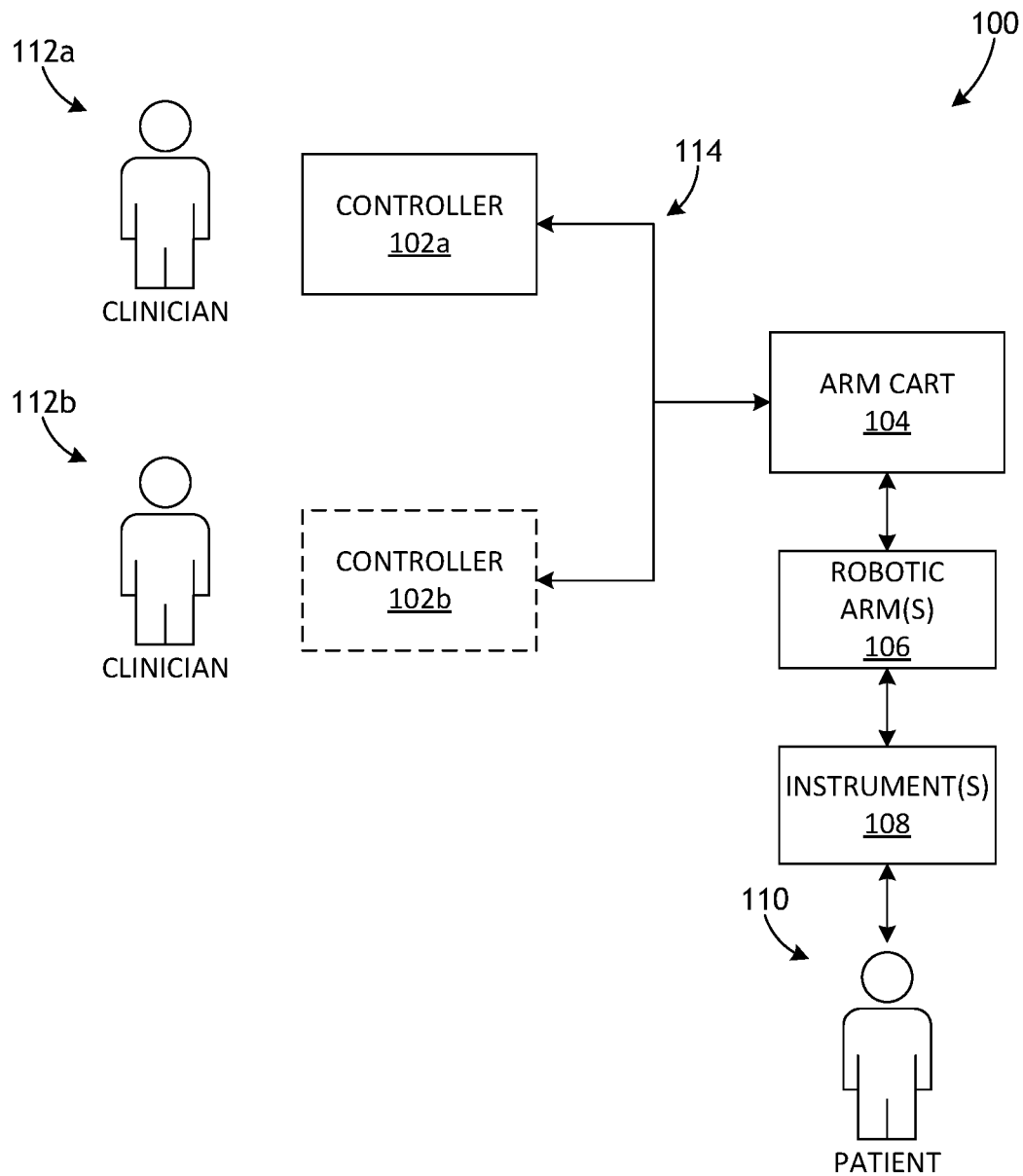
FIG. 1 is a block diagram of an example robotic surgical system that may incorporate some or all of the principles of the present disclosure.

FIG. 1 is a block diagram of an illustrative robotic surgical system that may incorporate some or all of the principles of the present disclosure. As illustrated, robotic surgical system 100 can include at least one master controller 102a and at least one arm cart 104. Arm cart 104 may be mechanically and/or electrically coupled to a robotic manipulator and, more particularly, to one or more robotic arms 106 or "tool drivers." Each robotic arm 106 may include and otherwise provide a location for mounting one or more surgical tools or instruments 108 for performing various surgical tasks on patient 110. Operation of robotic arm(s) 106 and instrument(s) 108 may be directed by clinician 112a (e.g., a surgeon) from master controller 102a.

In some embodiments, second master controller 102b (shown in dashed lines) operated by second clinician 112b may also direct operation of robotic arm(s) 106 and instrument(s) 108 in conjunction with first clinician 112a. For example, clinicians 112a and 112b may control different robotic arms 106 or, in some cases, complete control of robotic arms 106 may be passed between clinicians 112a and 112b. In some embodiments, additional arm carts (not shown) having additional robotic arms (not shown) may be utilized during a surgical procedure on patient 110, and these additional robotic arms may be controlled by one or more of master controllers 102a and 102b.

Arm cart 104 and master controllers 102a and 102b may be in communication with one another via communications link 114, which may be any type of wired or wireless telecommunication means configured to carry a variety of communication signals (e.g., electrical, optical, infrared, and the like) according to any communication protocol.

Master controllers 102a and 102b may include one or more physical controllers (not shown) that can be grasped by clinicians 112a and 112b and manipulated in space while viewing a procedure via a stereo display. The physical controllers may comprise manual input devices movable in multiple degrees of freedom, optionally including an actuatable handle for actuating instrument(s) 108. For example, actuation of instrument(s) 108 may include one or more of opening and closing opposing jaws, applying an electrical potential (current) to an electrode, or the like. Master controllers 102a and 102b can also include an optional feedback meter viewable by clinicians 112a and 112b via a display to provide a visual indication of various metrics of instrument(s) 108, such as the amount of force being applied to the surgical tool (e.g., via a cutting instrument or dynamic clamping member).

Example implementations of robotic surgical systems, such as robotic surgical system 100, are disclosed in U.S. Pat. No. 7,524,320, the contents of which are incorporated herein by reference in their entirety. Various aspects of such robotic surgical systems are not described in further detail herein beyond that needed to understand one or more of the various embodiments of robotic surgical apparatuses, systems, and methods disclosed herein.

Figure 2:
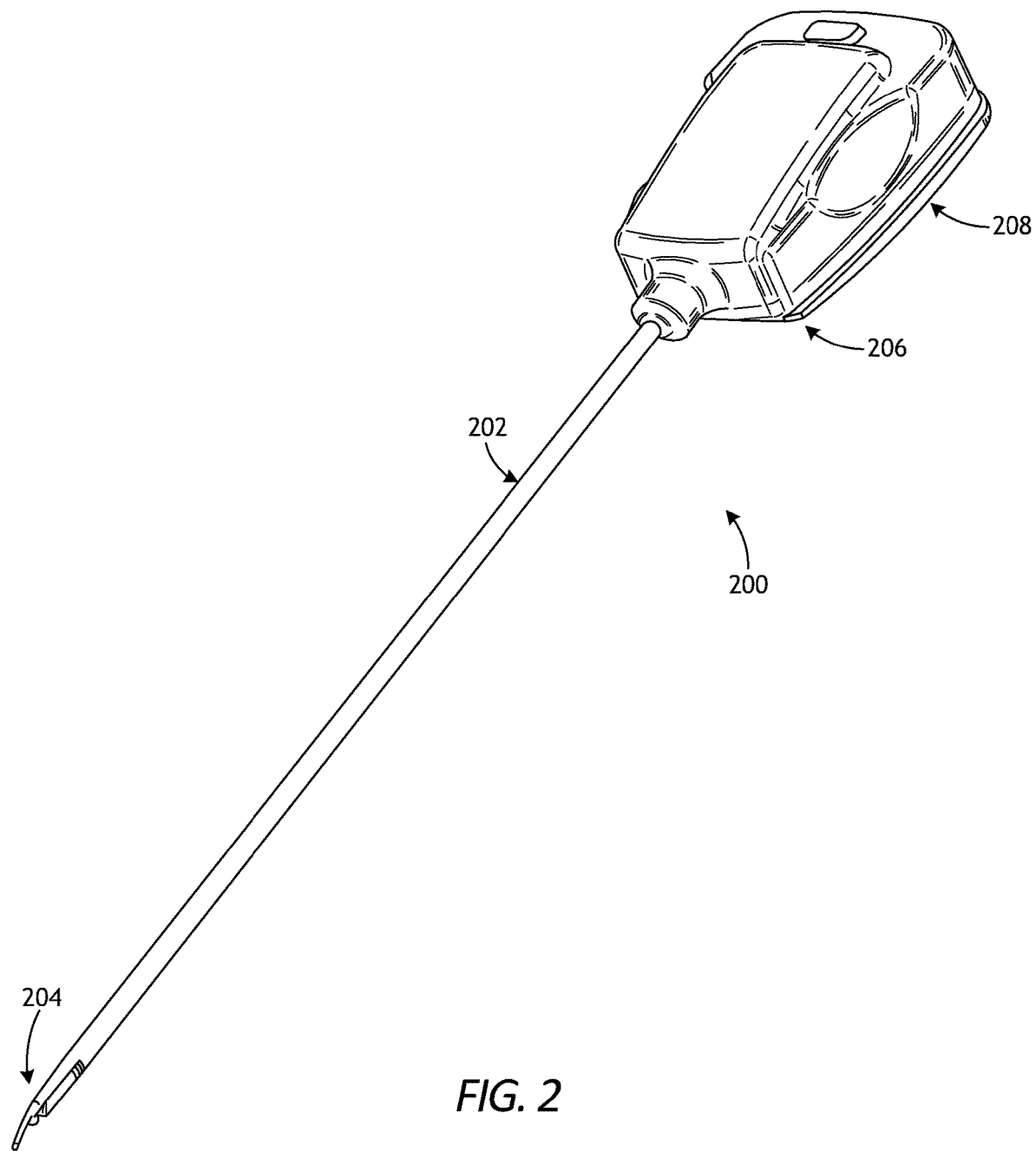
FIG. 2 is an isometric top view of an illustrative surgical tool that may incorporate some or all of the principles of the present disclosure.

FIG. 2 is an isometric top view of illustrative surgical tool 200 that may incorporate some or all of the principles of the present disclosure. Surgical tool 200 may be the same as or similar to instrument(s) 108 of FIG. 1 and, therefore, may be used in conjunction with robotic surgical system 100 of FIG. 1. Accordingly, surgical tool 200 may be designed for releasable coupling to robotic arm 106 (FIG. 1) of a robotic manipulator within robotic surgical system 100 or a similar robotic surgical system. Surgical tool 200 may be a surgical clip applier, according to some embodiments, as described in further detail in the present disclosure. Additional disclosure concerning surgical clip appliers is provided in U.S. Patent Application Publications 2016/0287252 and 2011/0224696, the contents of which are hereby incorporated by reference in their entirety.

While surgical tool 200 is described herein with reference to a robotic surgical system, it is to be appreciated that the principles of the present disclosure are similarly applicable to non-robotic MIS tools or, more specifically, manually operated MIS tools. Similarly, the principles of the present disclosure are also applicable to conventional laparoscopic and endoscopic surgical tools, according to some embodiments, both those incorporating a wrist and those that do not. Accordingly, the discussion provided herein relating to robotic surgical systems merely encompasses one example application of the presently disclosed embodiments.

As illustrated, surgical tool 200 includes elongate shaft 202, end effector 204 coupled to the distal end of elongate shaft 202, and drive housing 206 coupled to the proximal end of elongate shaft 202. The terms "proximal" and "distal" are defined herein relative to a robotic surgical system having an interface configured to mechanically and/or electrically couple surgical tool 200 (e.g., via drive housing 206) to a robotic manipulator. The term "proximal" refers to positioning of an element closer to the robotic manipulator or drive housing 206, and the term "distal" refers to positioning of an element closer to end effector 204 and thus further away from the robotic manipulator or drive housing 206. For non-robotically controlled MIS tools, the terms "proximal" and "distal" are defined similarly with respect to the location of engagement of the surgical tool by a surgeon. Moreover, use of directional terms such as above, below, upper, lower, upward, downward, left, right, and the like are used in the description herein in relation to the illustrative embodiments as they are depicted in the figures, the upward or upper direction being toward the top of the corresponding figure and the downward or lower direction being toward the bottom of the corresponding figure.

In applications where surgical tool 200 is used in conjunction with a robotic surgical system (e.g., system 100 of FIG. 1), drive housing 206 may include tool mounting portion 208 designed with features adapted to releasably couple surgical tool 200 to a robotic arm (e.g., robotic arm(s) 106 or "tool drivers" of FIG. 1) of a robotic manipulator. Tool mounting portion 208 may releasably attach (couple) drive housing 206 to a robotic arm in a variety of ways, such as clamping, clipping, slidable mating, or magnetic engagement. In some embodiments, tool mounting portion 208 may include an array of electrical connecting pins, which may be coupled to an electrical connection on the mounting surface of the robotic arm. While tool mounting portion 208 is described herein with reference to mechanical, electrical, and magnetic coupling elements, it should be understood that a wide variety of telemetry modalities may also be used, including infrared, inductive coupling, or the like.

Figure 3:
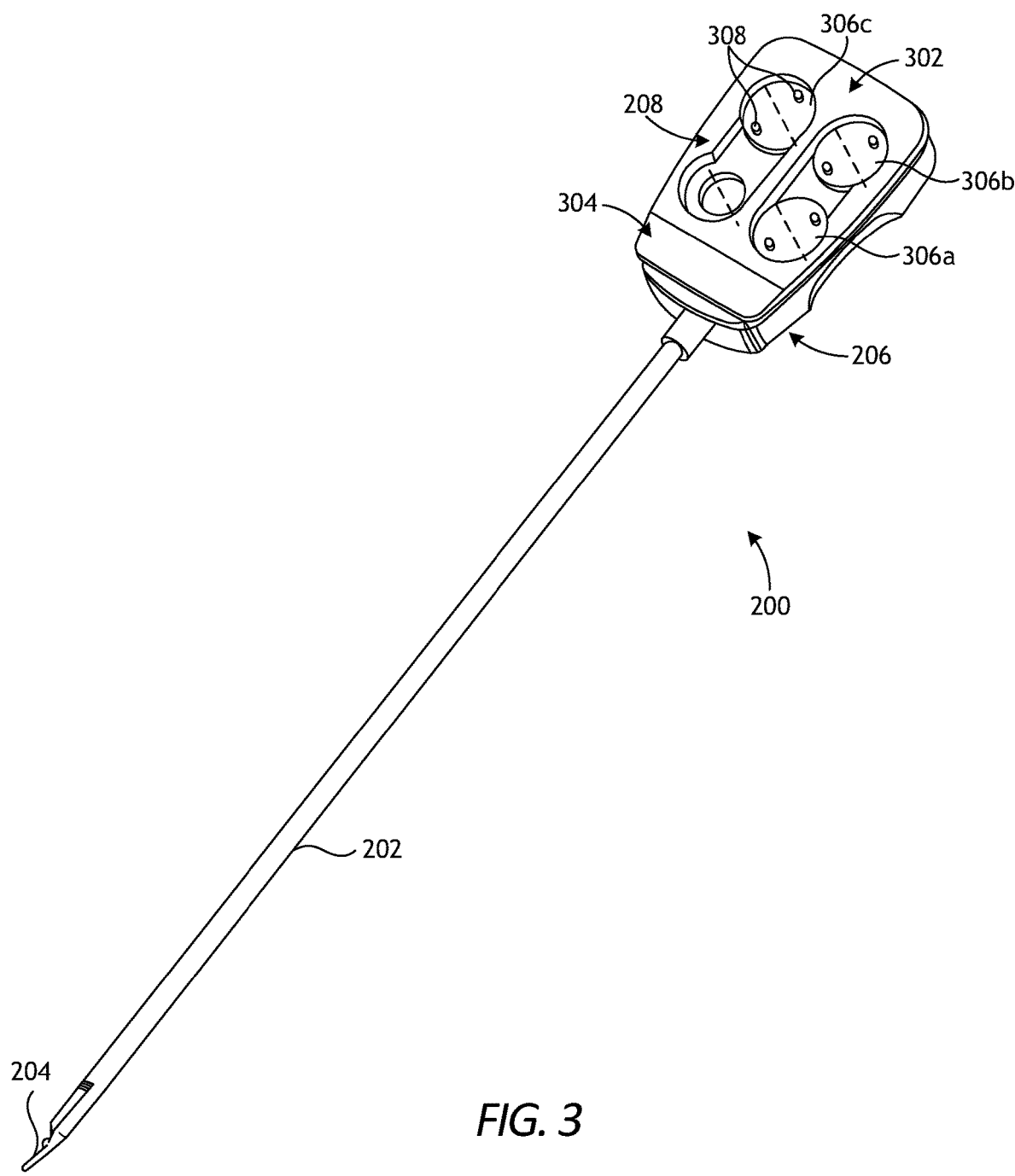
FIG. 3 is an isometric bottom view of the illustrative surgical tool of FIG. 2.

FIG. 3 is an isometric bottom view of illustrative surgical tool 200, which includes interface 302 that mechanically and/or electrically couples tool mounting portion 208 to a robotic manipulator. In various embodiments, tool mounting portion 208 includes tool mounting plate 304 that operably supports a plurality of drive inputs, shown as first drive input 306a, second drive input 306b, and third drive input 306c. While three drive inputs 306a-c are shown in FIG. 3, more or less than three may be employed, without departing from the scope of the present disclosure.

In the illustrated embodiment, each drive input 306a-c comprises a rotatable disc configured to align with and couple to a corresponding input actuator (not shown) of a corresponding robotic manipulator. Moreover, each drive input 306a-c provides or defines one or more surface features 308 configured to align with mating surface features provided on the corresponding input actuator. Surface features 308 can include, for example, various protrusions and/or indentations that are positioned to facilitate a mating engagement.

Figure 4:
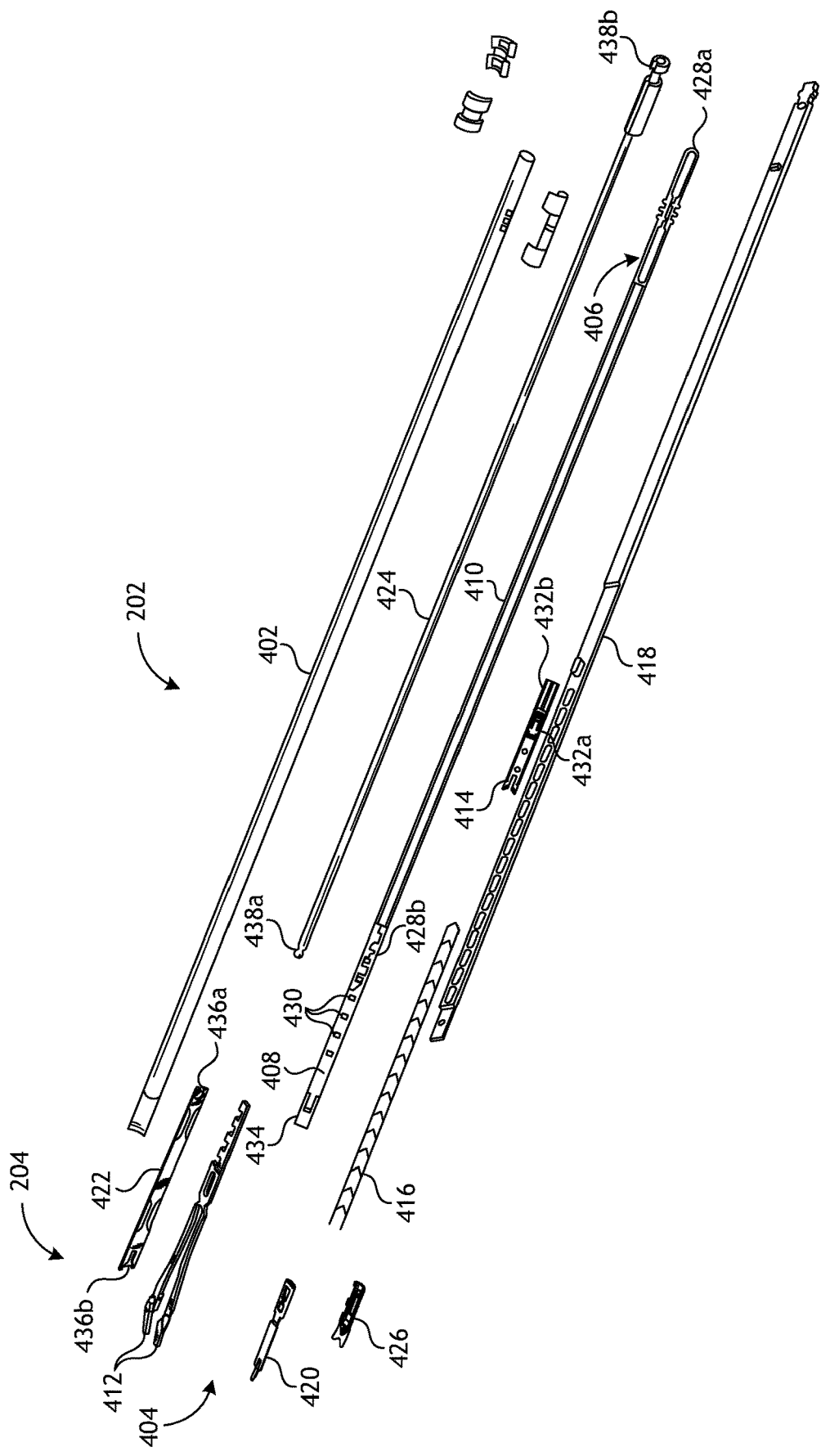
FIG. 4 is an exploded view of the elongate shaft and the end effector of the illustrative surgical tool of FIG. 2.

FIG. 4 is an exploded view of one example of elongate shaft 202 and end effector 204 within surgical tool 200, as depicted in FIGS. 2 and 3, according to one or more embodiments. In the illustrated embodiment, end effector 204 is configured as a surgical clip applier, the features and operational details of which are discussed hereinafter.

As illustrated in FIG. 4, elongate shaft 202 includes outer tube 402, which houses various components of elongate shaft 202 therein, including jaw retaining assembly 404. Jaw retaining assembly 404 includes jaw retainer shaft 406 with clip track 408 and push rod channel 410 formed thereon. End effector 204 also includes opposing jaw members 412 that are configured to mate to a distal end of clip track 408.

Elongate shaft 202 also includes a clip advancing assembly, which, in one example embodiment, can include feeder shoe 414 adapted to be slidably disposed within clip track 408. Feeder shoe 414 is designed to sequentially advance a series of surgical clips 416 positioned within clip track 408. Feedbar 418 is adapted to drive feeder shoe 414 through clip track 408 to affect advancement of surgical clips 416. Advancer component 420 is adapted to mate to a distal end of feedbar 418 for advancing a distal-most surgical clip into interposition between jaw members 412. Tissue stop 426 can mate to a distal end of clip track 408 to aid in positioning jaw members 412 relative to a surgical site.

Elongate shaft 202 further includes a clip forming assembly operable to urge jaw members 412 toward one another and thereby crimp (crush) the distal-most surgical clip placed into interposition between jaw members 412 by the clip advancement assembly (surgical clip interposition not shown in FIG. 4). As depicted in FIG. 4, the clip forming assembly comprises a camming assembly. The camming assembly includes cam 422 that slidably mates to jaw members 412, and push rod 424 that moves cam 422 longitudinally relative to jaw members 412.

Longitudinal movement of cam 422 may urge jaw members 412 to collapse together to affect crimping. It is to be appreciated that other structures to urge jaw members 412 together may be utilized in alternative embodiments of the present disclosure.

Jaw retainer shaft 406 is extendable within and couples to outer tube 402 at proximal end 428a, with distal end 428b being adapted to mate with jaw members 412. Push rod channel 410 formed on jaw retainer shaft 406 may be configured to slidably receive push rod 424, which is used to advance cam 422 over jaw members 412. Clip track 408 extends distally beyond distal end 428b of jaw retainer shaft 406 to allow a distal end of clip track 408 to be substantially aligned with jaw members 412.

Clip track 408 can include one or more openings 430 formed therein for receiving upper or "superior" tang 432a formed on feeder shoe 414 and adapted to be disposed within clip track 408. Clip track 408 can also include stop tang 434 formed thereon that is effective to become engaged by a corresponding stop tang (not shown in FIG. 4) formed on feeder shoe 414 to prevent movement of feeder shoe 414 beyond a specified distal-most position. To facilitate proximal movement of feeder shoe 414 within clip track 408, feeder shoe 414 can also include lower or "inferior" tang 432b formed on the underside thereof for allowing feeder shoe 414 to become engaged by feedbar 418 as feedbar 418 is moved distally. In use, each time feedbar 418 is moved distally, a detent formed in feedbar 418 engages inferior tang 432b and moves feeder shoe 414 distally a predetermined distance within clip track 408. Feedbar 418 can then be moved proximally to return to or near its initial position. The angle of inferior tang 432b allows inferior tang 432b to slide into the next detent formed in feedbar 418.

Jaw members 412 are movable (collapsible) relative to one another and are configured to receive therebetween a distal-most surgical clip from surgical clips 416. Jaw members 412 may each include a groove formed on opposed inner surfaces thereof for receiving the legs of an interposed surgical clip in alignment with jaw members 412. In the illustrated embodiment, jaw members 412 are biased to an open position and a force is required to urge opposed jaw members 412 toward one another to crimp the interposed surgical clip (not shown in FIG. 4). Jaw members 412 can also each include a cam track formed thereon for allowing cam 422 to slidably engage and move opposed jaw members 412 toward one another. Proximal end 436a of cam 422 is mateable with distal end 438a of push rod 424, and distal end 436b of cam 422 is adapted to engage and actuate jaw members 412. Proximal end 438b of push rod 424 is mateable with a closure link assembly associated with drive housing 206 for moving push rod 424 and cam 422 relative to jaw members 412.

Distal end 436b of cam 422 includes a camming channel or tapering recess formed therein for slidably receiving corresponding cam tracks provided by jaw members 412. In operation, cam 422 is advanced from a proximal position, in which jaw members 412 are spaced apart from one another, to a distal position, where jaw members 412 are collapsed to a closed position. As cam 422 is advanced over jaw members 412, the tapering recess at distal end 436b serves to urge jaw members 412 toward one another, thereby crimping an interposed surgical clip.

Figure 5:
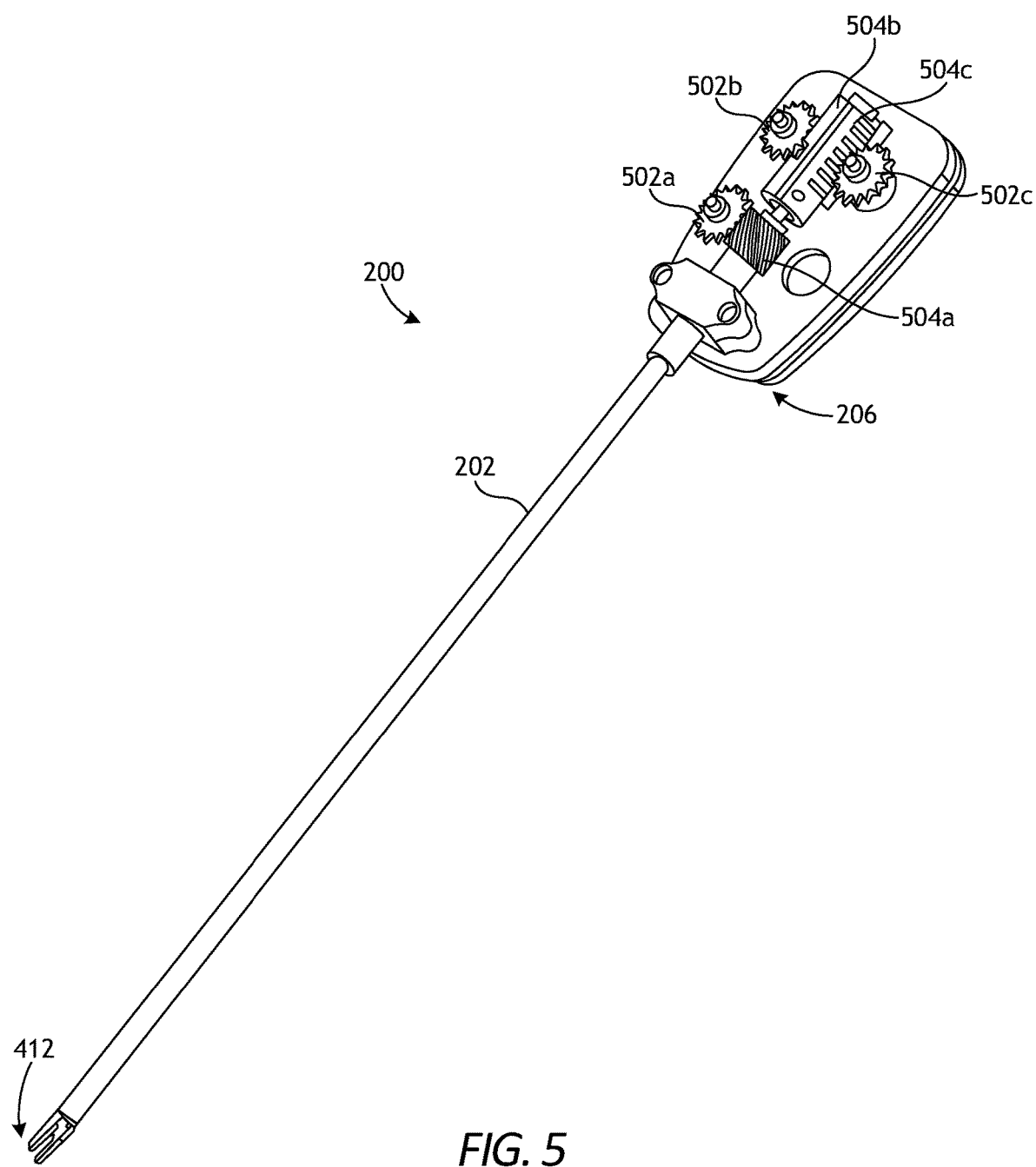
FIG. 5 is an exposed isometric view of the illustrative surgical tool of FIG. 2.

FIG. 5 is an exposed isometric view of illustrative surgical tool 200 of FIG. 2, according to one or more embodiments. In FIG. 5, the shroud or covering of drive housing 206 has been removed to reveal various internal component parts. As illustrated, surgical tool 200 may include first drive gear 502a, second drive gear 502b, and third drive gear 502c. First drive gear 502a may be operatively coupled to (or extend from) first drive input 306a (FIG. 3) such that actuation of first drive input 306a correspondingly rotates first drive gear 502a. Similarly, second and third drive gears 502b and 502c may be operatively coupled to (or extend from) corresponding second and third drive inputs 306b and 306c (FIG. 3), respectively, such that actuation of second and third drive inputs 306b and 306c correspondingly rotates second and third drive gears 502b and 502c, respectively.

First drive gear 502a may be configured to intermesh with first driven gear 504a, which is operatively coupled to elongate shaft 202. In the illustrated embodiment, first drive gear 502a and first driven gear 504a comprise mating helical gears. In operation, rotation of first drive gear 502a about a first axis correspondingly rotates first driven gear 504a about a second axis orthogonal to the first axis to control rotation of elongate shaft 202 in clockwise and counterclockwise directions based on the rotational direction of first drive gear 502a.

Second drive gear 502b may be configured to intermesh with second driven gear 504b (partially visible in FIG. 5), and third drive gear 502c may be configured to intermesh with third driven gear 504c. In the illustrated embodiment, second and third drive gears 502b and 502c and second and third driven gears 504b and 504c collectively comprise corresponding rack and pinion interfaces, where second and third driven gears 504b and 504c comprise the rack portion and second and third drive gears 502b and 502c comprise the pinion portion. Independent rotation of second and third drive gears 502b and 502c causes second and third driven gears 504b and 504c, respectively, to translate linearly relative to and independent of one another.

In at least one embodiment, actuation (rotation) of third drive gear 502c results in a distal-most surgical clip 416 (FIG. 4) being fed into interposition between jaws members 412. More particularly, third driven gear 504c may be operatively coupled to feedbar 418 (FIG. 4) and, upon rotation of third drive gear 502c in a first angular direction, third driven gear 504c may advance distally and correspondingly advance feedbar 418 a sufficient distance to advance surgical clip 416 into interposition between jaw members 412. Rotation of third drive gear 502c may be precisely controlled by an electrical and software interface to translate third driven gear 504c a sufficient distance to feed surgical clip 416 into jaw members 412.

Upon delivery of surgical clip 416 into interposition between jaw members 412, or after a predetermined amount of rotation of third drive gear 502c, rotation of third drive gear 502c may be reversed in a second angular direction to move third driven gear 504c linearly in a proximal direction, which correspondingly retracts feedbar 418 proximally. This process may be repeated as needed to deploy any remaining surgical clips 416 in a desired location.

Actuation of second drive gear 502b may urge jaw members 412 to close or collapse to affect crimping of an interposed surgical clip (not shown in FIG. 5). More particularly, second driven gear 504b may be coupled to proximal end 438b (FIG. 4) of push rod 424 (FIG. 4) and, upon actuation of second drive gear 502b in a first angular direction, second driven gear 504b may advance linearly in a distal direction and correspondingly drive push rod 424 distally. Distal advancement of push rod 424 may drive cam 422 over a portion of jaw members 412 to affect closure thereof and promote crimping of the interposed surgical clip.

Once the interposed surgical clip has been successfully deployed and crimped, rotation of second drive gear 502b in the opposite angular direction may move second driven gear 504b proximally. This action correspondingly moves push rod 424 and cam 422 proximally and permits jaw members 412 to open once again.

The processes for delivering surgical clips 416 into jaw members 412 and collapsing jaw members 412 to affect crimping are not limited to the actuation mechanisms and structures described herein. In alternative embodiments, for example, second and third driven gears 504b and 504c may instead comprise capstan pulleys configured to route and translate drive cables within elongate shaft 202. In such embodiments, the drive cables may be operatively coupled to one or more lead screws or other types of rotating members positioned within elongate shaft 202 near the distal end thereof. The drive cables may be similarly capable of advancing feedbar 418 to deliver surgical clips 416 into jaw members 412 and advancing cam 422 to collapse jaw members 412 to promote crimping.

Figure 6:
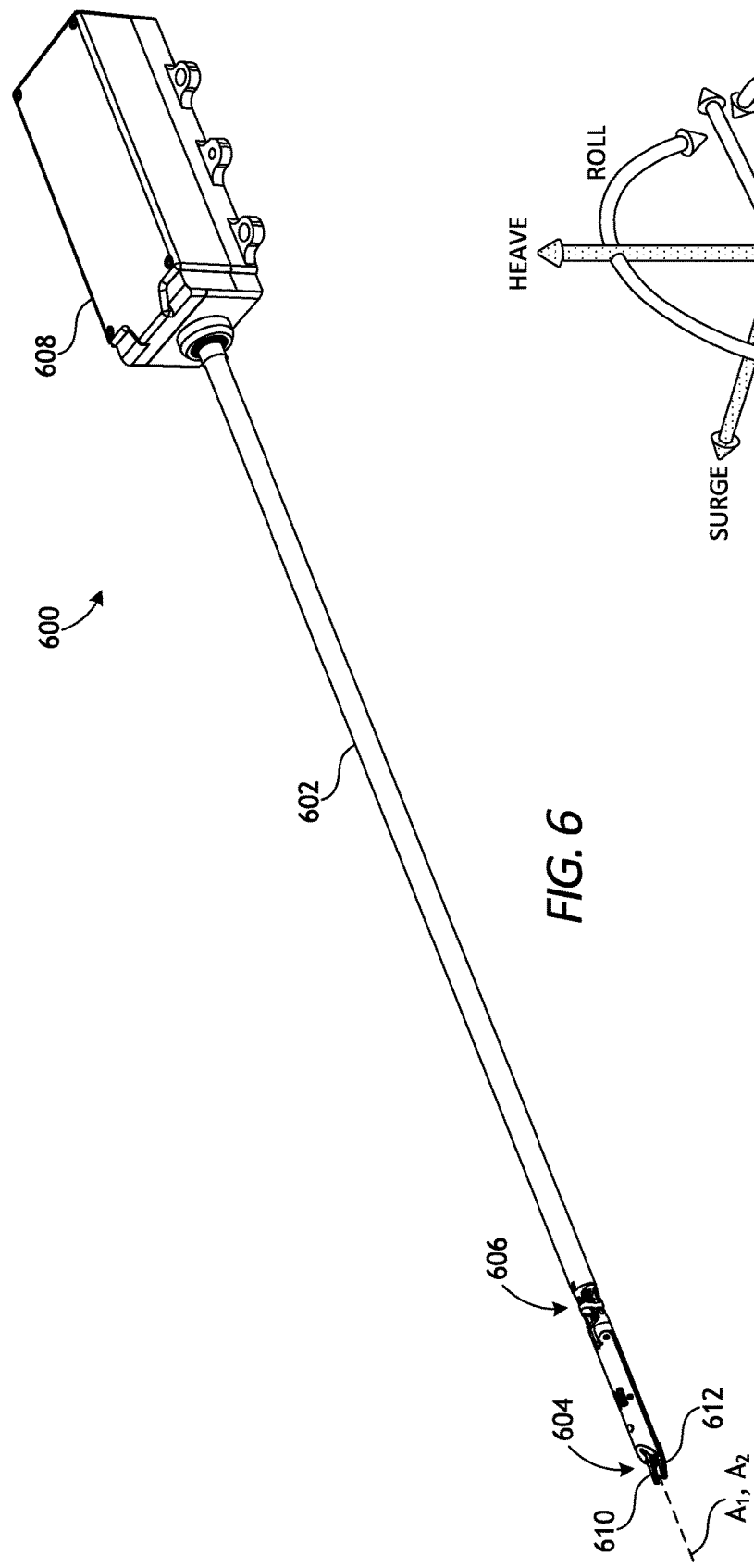
FIG. 6 is an isometric top view of another illustrative surgical tool that may incorporate some or all of the principles of the present disclosure.

FIG. 6 is an isometric top view of another illustrative surgical tool 600 that may incorporate some or all of the principles of the present disclosure. Similar to surgical tool 200 of FIG. 2, surgical tool 600 may be used in conjunction with robotic surgical system 100 of FIG. 1 or a similar robotic surgical system. As illustrated, surgical tool 600 includes elongate shaft 602, end effector 604 positioned at the distal end of elongate shaft 602, wrist 606 (alternately referred to as a "articulable wrist joint") that couples end effector 604 to the distal end of elongate shaft 602, and drive housing 608 coupled to the proximal end of elongate shaft 602. In some embodiments, elongate shaft 602, and hence end effector 604 coupled thereto, may be configured to rotate about longitudinal axis $A_1$.

As illustrated, end effector 604 comprises a surgical clip applier that includes opposing jaw members 610 and 612 configured to collapse toward one another to crimp a surgical clip in manner similar to that described in detail above for surgical tool 200. Wrist 606 comprises an articulable joint that facilitates pivoting movement of end effector 604 relative to elongate shaft 602 to position end effector 604 at a desired orientation and location relative to a surgical site. Housing 608 includes (contains) various actuation mechanisms designed to control articulation and operation of end effector 604.

Figure 7:
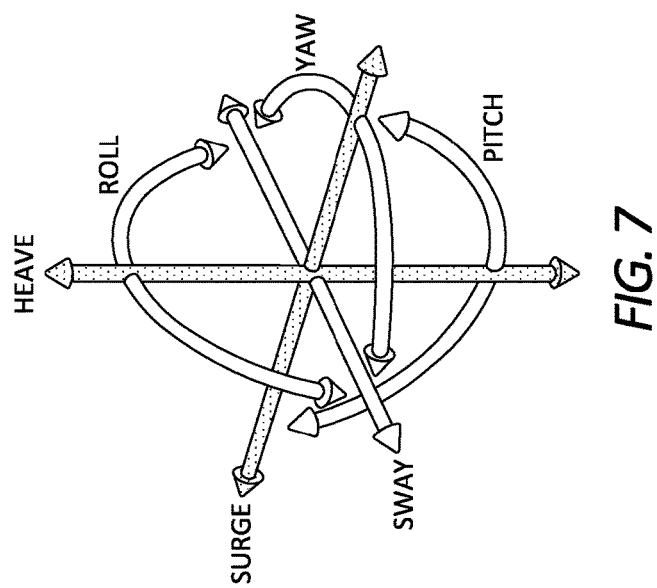
FIG. 7 illustrates the potential degrees of freedom through which a wrist of a surgical tool may be able to articulate (pivot).

FIG. 7 illustrates the potential degrees of freedom through which wrist 606 may be able to articulate (pivot). The degrees of freedom available to wrist 606 are represented by three translational variables (i.e., surge, heave, and sway), and by three rotational or orientation variables (i.e., Euler angles or roll, pitch, and yaw). The translational and rotational variables describe the position and orientation of a component of a surgical system (e.g., end effector 604) with respect to a given reference Cartesian frame or similar reference frame (e.g., a spherical coordinate system). As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

A pivoting motion may include pitch movement about a first axis of wrist 606 (e.g., X-axis), yaw movement about a second axis of wrist 606 (e.g., Y-axis), and combinations thereof to allow for 360° rotational movement of end effector 604 about wrist 606. In other applications, the pivoting motion can be limited to movement (rotation) in a single plane (e.g., only pitch movement about the first axis of wrist 606 or only yaw movement about second axis of wrist 606).

Referring again to FIG. 6, surgical tool 600 may include a plurality of drive cables (obscured in FIG. 6) that form part of a cable driven motion system, described in more detail below, that is configured to facilitate operation and articulation (movement) of end effector 604 relative to elongate shaft 602. For example, selectively moving one or more of the drive cables can actuate end effector 604 and thereby collapse jaw members 610 and 612 toward each other. Moreover, moving one or more of the drive cables can also transition end effector 604 between an unarticulated position and an articulated position. End effector 604 is depicted in FIG. 6 in the unarticulated position where longitudinal axis $A_2$ of end effector 604 is substantially aligned with longitudinal axis $A_1$ of elongate shaft 602, such that end effector 604 is at a substantially zero angle relative to elongate shaft 602. In the articulated position, longitudinal axes $A_1$ and $A_2$ are angularly offset from each other such that end effector 604 is at a non-zero angle relative to elongate shaft 602.

Figure 8:
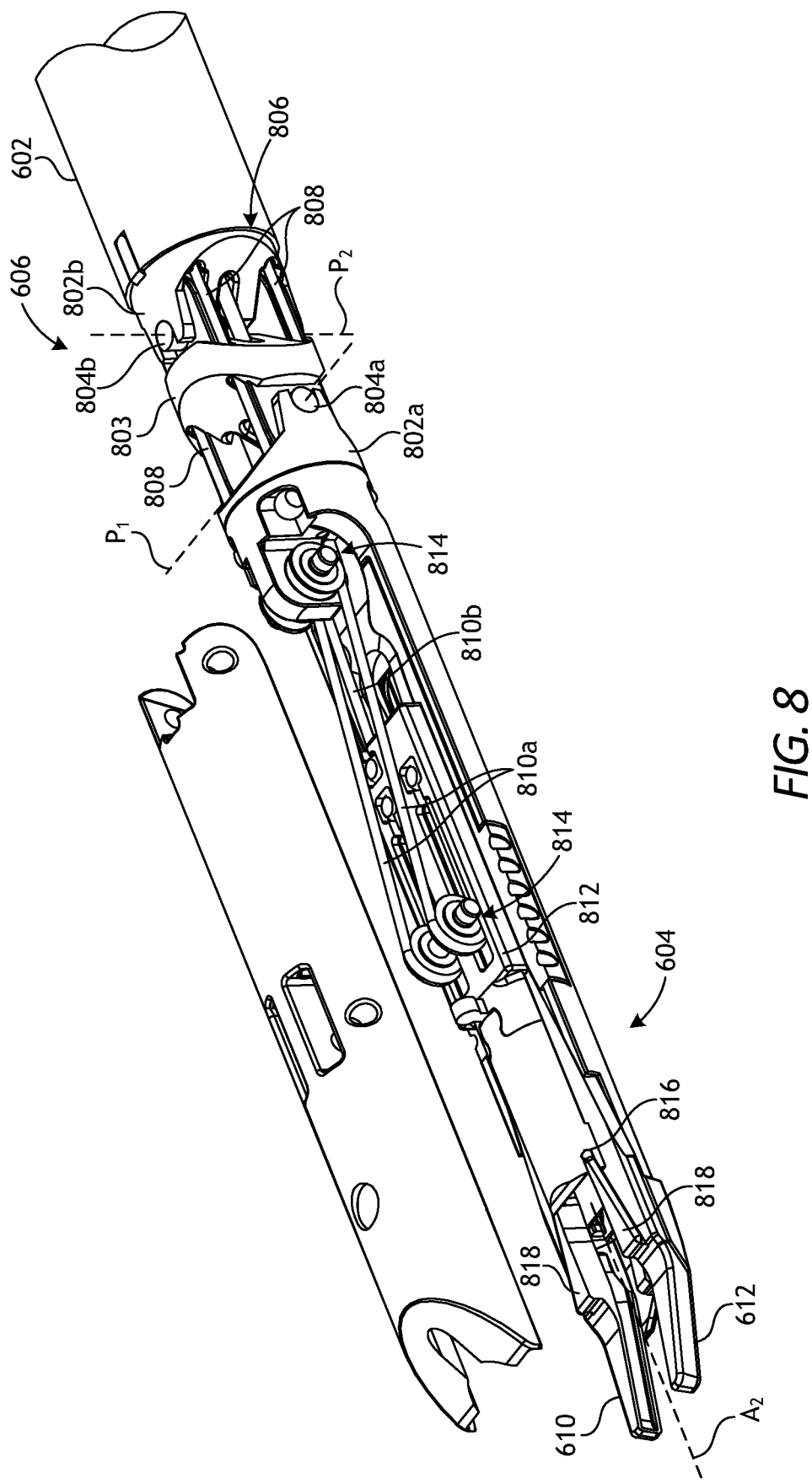
FIG. 8 is an enlarged, partially exploded isometric view of the distal end of the illustrative surgical tool of FIG. 6.

FIG. 8 is an enlarged isometric view of the distal end of illustrative surgical tool 600 of FIG. 6. More specifically, FIG. 8 depicts an enlarged and partially exploded view of end effector 604 and wrist 606. Wrist 606 operatively couples end effector 604 to elongate shaft 602. To achieve operable coupling, wrist 606 includes distal clevis 802a, proximal clevis 802b, and spacer 803 interposed between distal clevis 802a and proximal clevis 802b. End effector 604 is coupled to distal clevis 802a, and distal clevis 802a is rotatably mounted to spacer 803 at first axle 804a. Spacer 803 is rotatably mounted to proximal clevis 802b at second axle 804b, and proximal clevis 802b is coupled to distal end 806 of elongate shaft 602.

Wrist 606 provides first pivot axis $P_1$ that extends through first axle 804a and second pivot axis $P_2$ that extends through second axle 804b. First pivot axis $P_1$ is substantially perpendicular (orthogonal) to longitudinal axis $A_2$ of end effector 604, and second pivot axis $P_2$ is substantially perpendicular (orthogonal) to both longitudinal axis $A_2$ and first pivot axis $P_1$. Movement about first pivot axis $P_1$ provides "pitch" articulation of end effector 604, and movement about second pivot axis $P_2$ provides "yaw" articulation of end effector 604.

A plurality of drive cables 808 extend longitudinally within elongate shaft 602, pass through wrist 606 and are operably coupled to a component of end effector 604. Drive cables 808 form part of the cable driven motion system referenced in brief above, and may be referred to herein and otherwise be characterized as cables, bands, lines, cords, wires, ropes, strings, twisted strings, elongate members, and the like. Drive cables 808 may be made from a variety of materials including, but not limited to, metal (e.g., tungsten, stainless steel, and the like) or a polymer.

Drive cables 808 extend proximally from end effector 604 to drive housing 608 (FIG. 6), where they are operatively coupled to various actuation mechanisms or devices housed (contained) therein to facilitate longitudinal movement (translation) of drive cables 808. Selective actuation of drive cables 808 may cause end effector 604 to articulate (pivot) relative to elongate shaft 602. Moving a given drive cable 808 constitutes applying tension (i.e., a pull force) to the given drive cable 808 in a proximal direction, which causes the given drive cable 808 to translate proximally and thereby cause end effector 604 to move (articulate) relative to elongate shaft 602.

One or more actuation cables, shown as first actuation cables 810a and second actuation cables 810b, may also extend longitudinally within elongate shaft 602 and pass through wrist 606, where they are operably coupled to a component of end effector 604. First and second actuation cables 810a and 810b may be similar in nature to drive cables 808 and also form part of the above-referenced cable driven motion system. Selectively actuating first and second actuation cables 810a and 810b causes end effector 604 to actuate, such as collapsing jaw members 610 and 612 to crimp an interposed surgical clip (not shown).

More specifically, first and second actuation cables 810a and 810b may be operatively coupled to cam 812 that is slidably engageable with jaw members 610 and 612. One or more pulleys 814 may receive and redirect first actuation cables 810a for engagement with cam 812. As such, longitudinal movement of first actuation cables 810a correspondingly moves cam 812 distally relative to jaw members 610 and 612. The distal end of cam 812 includes a tapering recess or camming channel 816 formed therein for slidably receiving corresponding cam tracks 818 provided by jaw members 610 and 612. As cam 812 is advanced distally, camming channel 816 pushes (collapses) jaw members 610 and 612 toward one another, thereby crimping an interposed surgical clip (not shown). Longitudinal movement of second actuation cables 810b (one shown) may pull cam 812 proximally, thereby allowing jaw members 610 and 612 to open again to receive another surgical clip.

Although not expressly depicted in FIG. 8, an assembly including, for example, a feedbar, a feeder shoe, and a clip track may be included at or near end effector 604 to facilitate feeding of surgical clips into jaw members 610 and 612. These elements may be similar to those shown in surgical tool 200 and described in more detail hereinabove. In some embodiments, the feedbar (or a connecting member) may be flexible and extend through wrist 606.

Figure 9:
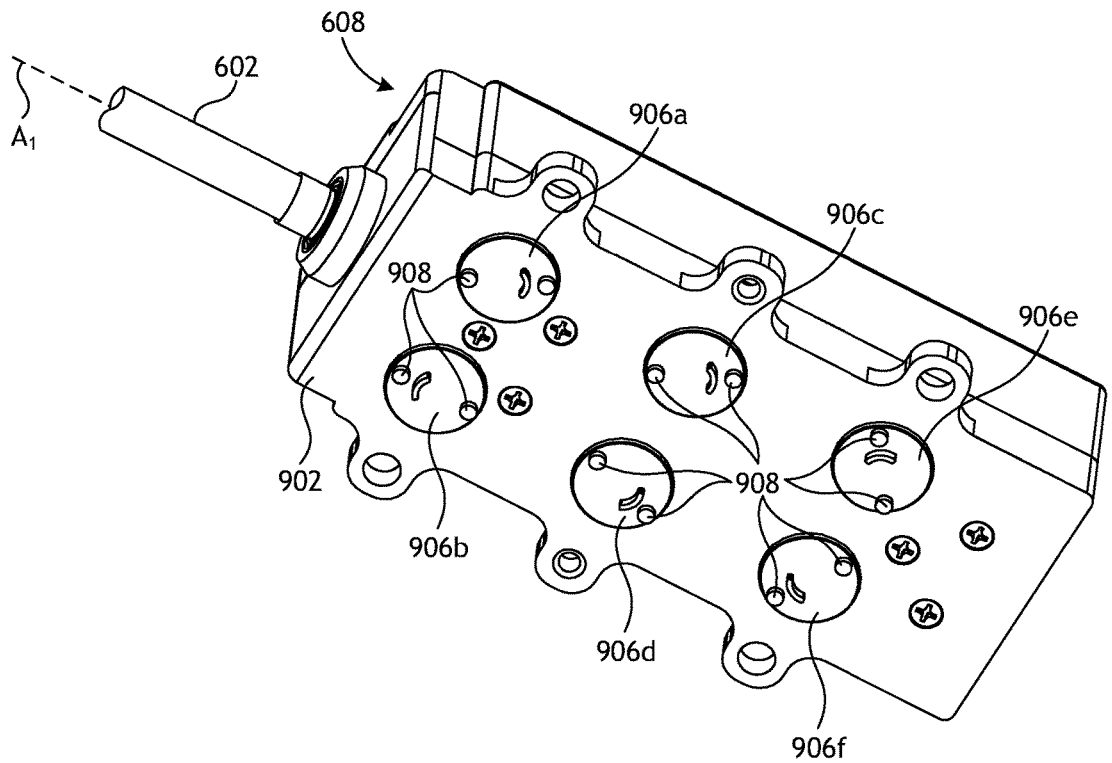
FIG. 9 is a bottom view of the drive housing of the illustrative surgical tool of FIG. 6.

FIG. 9 is a bottom view of drive housing 608 of illustrative surgical tool 600, according to one or more embodiments. As illustrated, drive housing 608 may include tool mounting interface 902 used to operatively couple drive housing 608 to a robotic manipulator. Without limitation, tool mounting interface 902 may mechanically, magnetically, and/or electrically couple drive housing 608 to the robotic manipulator.

Tool mounting interface 902 further includes and supports a plurality of drive inputs, shown in FIG. 9 as drive inputs 906a, 906b, 906c, 906d, 906e, and 906f. Each drive input 906a-f may comprise a rotatable disc configured to align with and couple to a corresponding input actuator (not shown) of a corresponding robotic manipulator, similar to those described above for surgical tool 200. Each drive input 906a-f may further provide or define one or more surface features 908 configured to align with mating features provided on the corresponding input actuator. The surface features 908 can include, for example, various protrusions and/or indentations that facilitate a mating engagement.

In some embodiments, actuation of first drive input 906a may control rotation of elongate shaft 602 about longitudinal axis $A_1$. Depending on the rotational direction of first drive input 906a, elongate shaft 602 may be rotated clockwise or counterclockwise. Rotation capabilities of elongate shaft 602 optionally may be omitted in some embodiments. In some embodiments, selective actuation of second and/or third drive inputs 906b and 906c may cause movement (axial translation) of first and/or second actuation cables 810a and 810b (FIG. 8), which correspondingly may cause cam 812 (FIG. 8) to move and crimp an interposed surgical clip between jaw members 610 and 612, as generally described above. In some embodiments, actuation of fourth drive input 906d may feed a surgical clip into interposition between jaw members 610 and 612 (e.g., by longitudinally translating and retracting a feedbar). In some embodiments, actuation of fifth and sixth drive inputs 906e and 906f may cause movement (axial translation) of drive cables 808 (FIG. 8) to result in articulation of end effector 604. Each of drive inputs 906a-f may be actuated independently based on user inputs communicated to a robotic manipulator coupled to tool mounting interface 902. The user inputs may be received via a computer system incorporated into the robotic surgical system.

Figure 10:
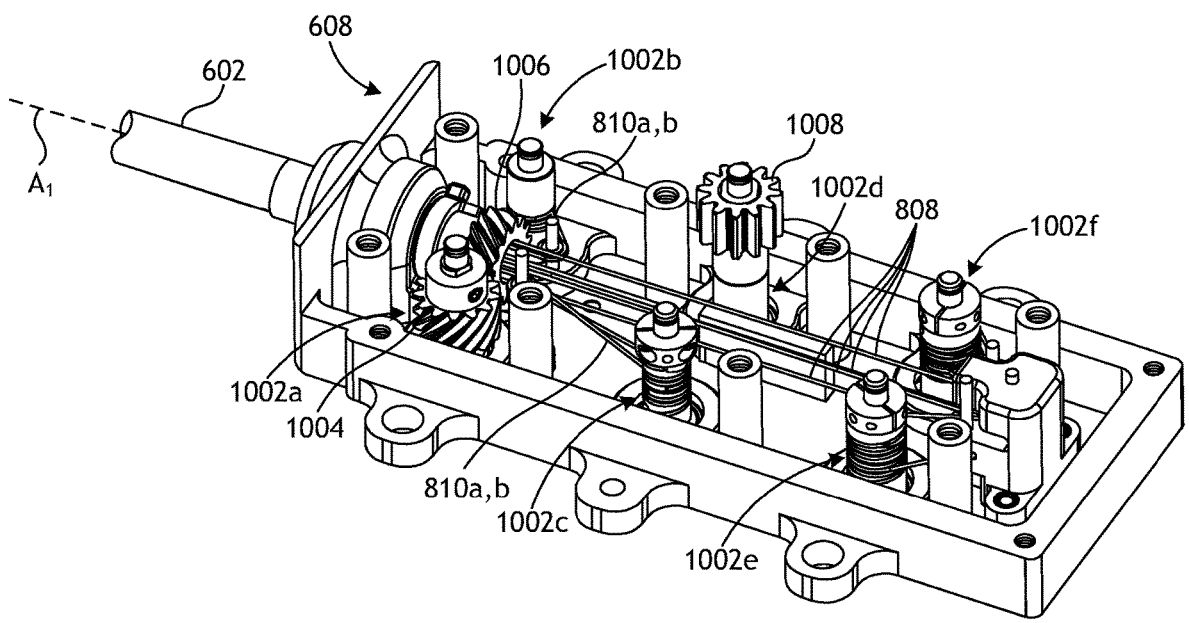
FIG. 10 is an isometric exposed view of the interior of the drive housing of the illustrative surgical tool of FIG. 6.

FIG. 10 is an isometric exposed view of the interior of drive housing 608 of illustrative surgical tool 600, according to one or more embodiments. Several component parts that may otherwise be contained within drive housing 608 are not shown in FIG. 10 to allow for clearer viewing of the depicted component parts and to facilitate discussion thereof.

As illustrated in FIG. 10, drive housing 608 contains first capstan 1002a, which is operatively coupled to or extends from first drive input 906a (FIG. 9), such that actuation of first drive input 906a results in rotation of first capstan 1002a. Helical drive gear 1004 is coupled to or forms part of first capstan 1002a and is configured to interact with driven gear 1006 that is operatively coupled to elongate shaft 602, such that rotation of driven gear 1006 may correspondingly rotate elongate shaft 602. Accordingly, rotation of helical drive gear 1004 (via actuation of first drive input 906a) drives driven gear 1006 and thereby affects rotation of elongate shaft 602 about longitudinal axis $A_1$.

When rotation of elongate shaft 602 is unnecessary or undesired in alternate configurations of surgical tool 600, the components engageable with first drive input 906a may be configured differently. For example, first capstan 1002a may be configured to translate a cable longitudinally within elongate shaft 602 instead of promoting rotation of elongate shaft 602 as depicted. The cable may aid in actuating other various components within end effector 604.

Drive housing 608 also includes second and third capstans 1002b and 1002c operatively coupled to or extending from second and third drive inputs 906b and 906c (FIG. 9), respectively, such that actuation of second and/or third drive inputs 906b and 906c results in rotation of second and/or third capstans 1002b and 1002c. Second and third capstans 1002b and 1002c comprise capstan pulleys operatively coupled to first and second actuation cables 810a and 810b (FIG. 8), respectively, such that rotation of either second capstan 1002b or third capstan 1002c actuates (longitudinally moves) a corresponding one of first actuation cable 810a or second actuation cable 810b. Accordingly, selective rotation of second and/or third capstans 1002b and 1002c via actuation of second and/or third drive inputs 906b and 906c, respectively, causes movement (axial translation) of first and/or second actuation cables 810a and 810b, resulting in movement of cam 812 and crimping of an interposed surgical clip between jaw members 610 and 612.

Drive housing 608 further includes fourth capstan 1002d, which is operatively coupled to or extends from fourth drive input 906d (FIG. 9), such that actuation of fourth drive input 906d results in rotation of fourth capstan 1002d. Spur gear 1008 is coupled to or forms part of fourth capstan 1002d and is configured to mesh and interact with a rack gear (not shown) also contained within drive housing 608. The rack gear may be operatively coupled to a feedbar (or another connecting member), which facilitates operation of a feeder shoe and associated clip track to feed surgical clips into jaw members 610 and 612 (FIGS. 6 and 8). Accordingly, rotation of spur gear 1008 (via actuation of fourth drive input 906d) may control the feedbar and thereby facilitate loading of surgical clips into jaw members 610 and 612 as desired.

Drive housing 608 further includes fifth and sixth capstans 1002e and 1002f operatively coupled to or extending from fifth and sixth drive inputs 906e and 906f (FIG. 9), respectively, such that actuation of fifth and sixth drive inputs 906e and 906f results in rotation of fifth and sixth capstans 1002e and 1002f. Fifth and sixth capstans 1002e and 1002f each comprise capstan pulleys operatively coupled to drive cables 808 (FIG. 8), such that rotation of fifth and/or sixth capstans 1002e and 1002f actuates (longitudinally moves) a corresponding one of drive cables 808. Accordingly, selective rotation of fifth and/or sixth capstans 1002e and 1002f via actuation of fifth and/or sixth drive inputs 906e and 906f, respectively, may affect movement (axial translation) of drive cables 808 and thereby articulate (pivot) end effector 604 relative to elongate shaft 602.

The principles and features of the present disclosure may be incorporated within surgical tools 200 and 600 described hereinabove, as well as within similar surgical tools, to facilitate feeding and more efficient packing of surgical clips in surgical clip appliers, including robotic clip appliers, laparoscopic clip appliers, endoscopic clip appliers, and similar surgical tools, particularly surgical tools incorporating an articulable wrist. As will be appreciated by one having ordinary skill in the art and the benefit of the present disclosure, some or all of the principles and features of surgical tools 200 and 600 may be modified to incorporate the various surgical clip feeding and packing features described hereinafter. Accordingly, example surgical tools incorporating the principles, features and benefits of the present disclosure may incorporate any combination of geared actuators, capstan pulleys, cable actuators, feedbars, cams, and similar elements, such as those described above in reference to FIGS. 1-10, without departing from the scope of the present disclosure. Such components may be operably connected to and/or contained within an end effector incorporating the principles described hereinafter.

According to various embodiments, end effectors of surgical tools of the present disclosure may house multiple surgical clips at a location distal to a wrist or similar articulation joint (e.g., wrist 606 in FIG. 6). That is, surgical tools and end effectors of the present disclosure may incorporate (store) the surgical clips on a side of the wrist that is closer to the jaw members of a surgical clip applier rather than nearer to the drive housing or other location of engagement of a surgical tool. As such, end effectors of the present disclosure avoid the issue of having to transport (convey) surgical clips through the wrist to affect clip feeding to the jaw members of a surgical clip applier. It is to be appreciated, however, that the principles of the present disclosure may be similarly employed within surgical tools that do not incorporate a wrist or similar articulation joint, without departing from the scope of the disclosure.

More particularly, end effectors of the present disclosure may feature surgical clips having an arcuate (curved) crown-to-tail profile, which may facilitate more efficient clip packing within a given longitudinal space. Such surgical clips may be referred to hereinafter as "arcuate surgical clips." Arcuate surgical clips may be nested together in series within end effectors of the present disclosure, such that a given (first) surgical clip abuts a complementary surface along the curvature profile of an adjacent (second) surgical clip. Nesting of the surgical clips in this manner allows a greater number of surgical clips to be close packed in a given longitudinal space compared to crown-to-tail packing of the surgical clips in a coplanar arrangement. The clip curvature (i.e., radius of curvature) may be selected to alter the number of arcuate surgical clips that may be packed in a given longitudinal space, and to facilitate clip feeding as well. Further, provided that the arcuate surgical clips are located below a transparent housing in the end effector, the number of remaining surgical clips may be viewed endoscopically when arranged in the nested configuration, which may aid in planning how to complete a surgical procedure.

Similarly, end effectors of the present disclosure may feature arcuate jaw members as well. The arcuate jaw members may have a curved profile (shape) similar to (complementary to) that of the arcuate surgical clips in order to receive, advance, and crimp the arcuate surgical clips therein. As used herein in reference to arcuate jaw members, the term "curved profile" refers to the shape of the arcuate jaw members as viewed from the side where the jaw members align with (eclipse) one another. Similarly, as used herein in reference to arcuate surgical clips, the term "curved profile" refers to the shape of the arcuate surgical clips as viewed from the side where the clip legs align with (eclipse) one another. Advantageously, the arcuate jaw members may likewise decrease the overall size (length) of the end effector that undergoes articulation during use (e.g., in comparison to planar jaw members configured to receive and crimp substantially planar surgical clips). As such, arcuate jaw members, in addition to facilitating compatibility with the arcuate surgical clips, may improve articulation accuracy of an end effector where they are present. In addition, arcuate jaw members may be further advantageous for offering an improved field of view and greater tissue access for a surgeon during a surgical procedure.

Thus, the use of arcuate surgical clips according to various embodiments of the present disclosure can avoid issues associated with clip feeding through a wrist while simultaneously avoiding significant impacts to the diameter and/or length of an end effector, thereby not degrading the attainable level of articulation accuracy.

In addition, according to some embodiments, the arcuate surgical clips may be incorporated in a clip magazine (cartridge) that may be removably coupled to the end effector, which may provide further advantages. For example, interchanging clip magazines during a surgical procedure may allow arcuate surgical clips of different size and/or type to be dispensed from a single surgical tool, thereby potentially expanding the breadth of surgical techniques available to a medical practitioner. Magazine replacement also increases the number of surgical clips available during a surgical procedure should a single magazine hold an insufficient number of surgical clips. Likewise, magazine replacement may also enable multiple uses of a non-consumable surgical tool by facilitating ready reloading of the end effector with surgical clips. In other embodiments of the present disclosure, however, arcuate surgical clips may be incorporated within a single-use surgical tool, with or without using a magazine or similar structure, while still enjoying certain advantages described herein.

Figure 11:
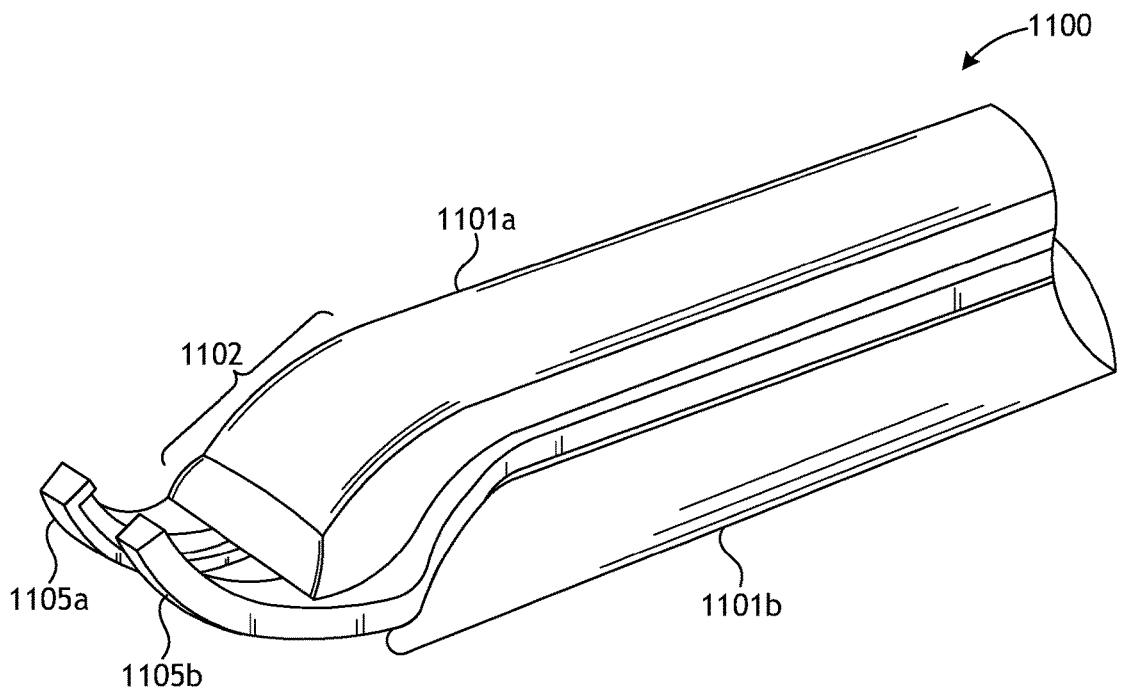
FIGS. 11-13 are isometric views of an end effector incorporating arcuate jaw members.
Figure 12:
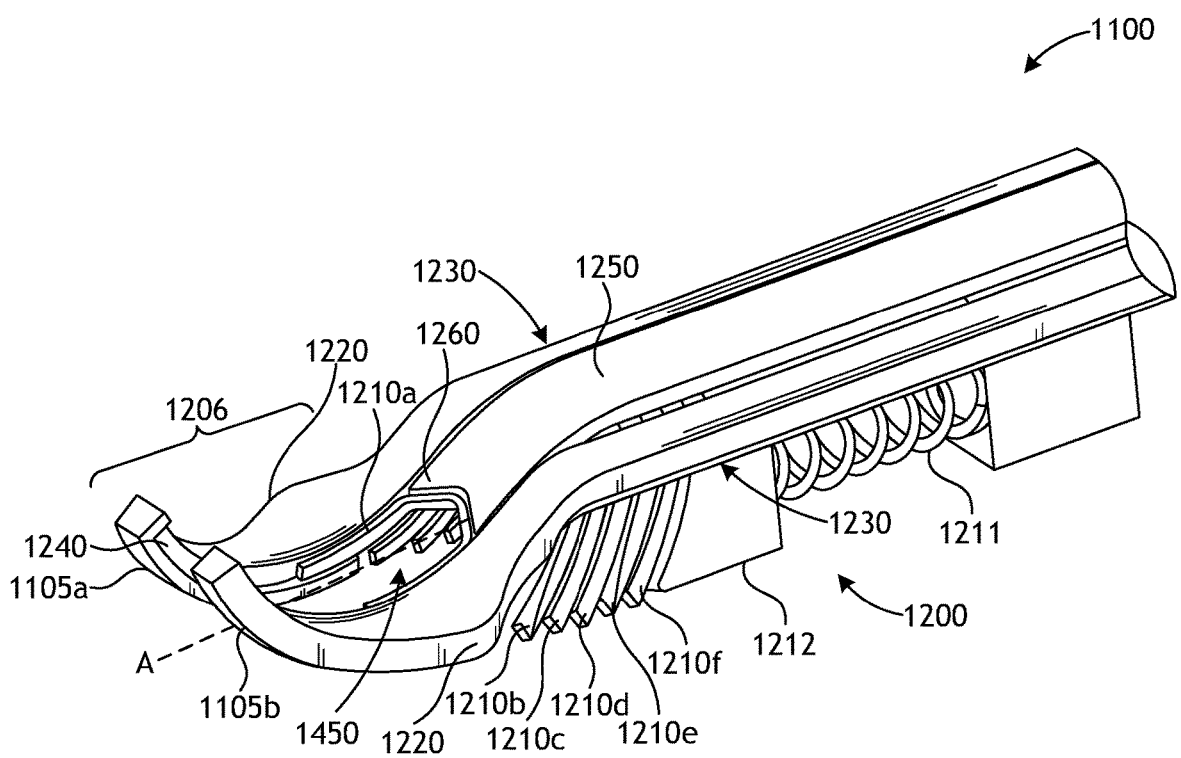
Figure 13:
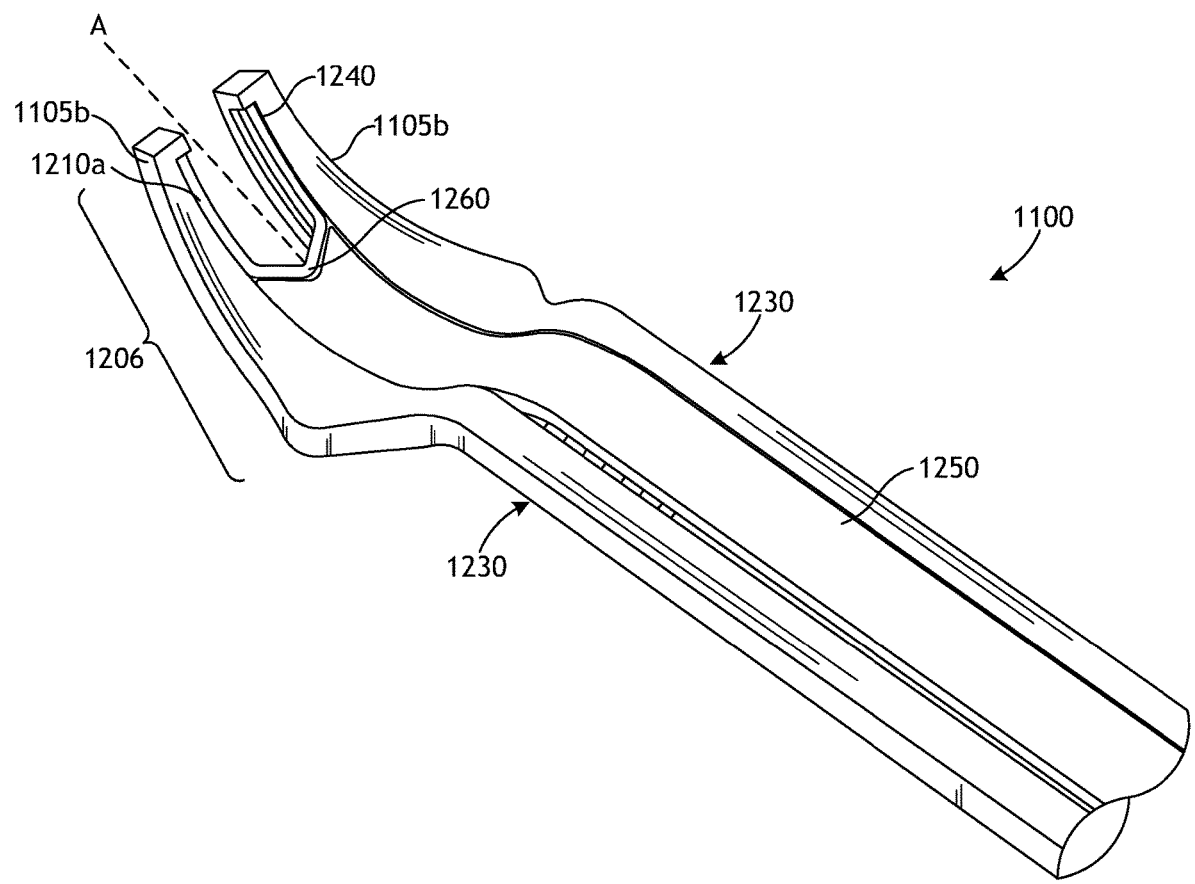

FIGS. 11-13 show various views of end effector 1100, which may incorporate arcuate surgical clips therein. As depicted, FIGS. 11-13 show the portion of end effector 1100 distal to a wrist (not shown in FIGS. 11-13). It is to be appreciated that end effector 1100 may incorporate a wrist similar to wrist 606 (FIG. 6), as well as other previously described features and components suitable for articulating, rotating and/or actuating the components comprising end effector 1100. As such, for example, it is to be appreciated that drive inputs and capstans similar to drive inputs 906a-f (FIG. 9) and capstans 1002a-f (FIG. 10) and their associated features may be in communication with one or more of the various components depicted in FIGS. 11-13 in order to affect operation thereof. Moreover, it is to be further appreciated that end effector 1100 may be employed in non-wristed surgical tools as well.

FIG. 11 shows an isometric view of the exterior of end effector 1100, which includes upper housing 1101a and lower housing 1101b. Upper and lower housings 1101a and 1101b may function as a shroud covering the internal components of end effector 1100, which are described in further detail hereinafter. At least upper housing 1101a includes tapered section 1102, which may include an internal tapered surface to aid in positioning arcuate surgical clips (not visible in FIG. 11) for subsequent interpositioning between jaw members 1105a and 1105b, as also described hereinafter. In some embodiments, the inner surface (internal tapered surface) of upper housing 1101a within tapered section 1102 may define a portion of a channel (not visible in FIG. 11), through which the arcuate surgical clips may travel in the course of becoming interposed between jaw members 1105a and 1105b. In some or other embodiments, tapered section 1102 may aid in directing the arcuate surgical clips to jaw members 1105a and 1105b, which have a curved profile (i.e., arcuate shape) similar to that of the arcuate surgical clips. Jaw members 1105a and 1105b may be referred to hereinafter as "arcuate jaw members" 1105a and 1105b. According to such embodiments, the inner surface of tapered section 1102 may serve as a forward stop for the distal-most arcuate surgical clip before further distal advancement takes place.

FIG. 12 is an exposed isometric view of end effector 1100, in which upper and lower housings 1101a and 1101b (FIG. 11) have been removed to show the placement of various internal components. As illustrated, end effector 1100 includes surgical clip feeder 1200, which is loaded with arcuate surgical clips 1210b-f that are nested together along corresponding curved surfaces thereof. In the configuration depicted in FIG. 12, arcuate surgical clip 1210a has already been ejected from the nesting arrangement in surgical clip feeder 1200 and is partially advanced distally toward jaw members 1105a and 1105b. Accordingly, arcuate surgical clip 1210a is positioned to become fully interposed between jaw members 1105a and 1105b upon further distal advancement, as described hereinafter. Prior to its ejection from surgical clip feeder 1200, arcuate surgical clip 1210a is similarly nested with arcuate surgical clips 1210b-f, as shown below in FIG. 14.

Arcuate surgical clips 1210a-f are arranged such that the crowns of arcuate surgical clips 1210a-f are located nearer to upper housing 1101a (FIG. 11) than are the corresponding tails (i.e., the end of each leg). As such, arcuate surgical clips 1210a-f are nested or positioned at a non-zero packing angle with respect to longitudinal axis A of end effector 1100. The non-zero packing angle depicted in FIG. 12 is for purposes of illustration and should not be considered limiting. The packing angle may depend, for example, on the crown-to-tail length of the arcuate surgical clips, the radius of curvature, and the inner diameter of the end effector. According to various embodiments, the non-zero packing angle with respect to longitudinal axis A may range between about 1 degree and about 89 degrees. In more specific embodiments, the non-zero packing angle may range between about 10 degrees and about 70 degrees, or between about 15 degrees and about 50 degrees, or between about 20 degrees and about 45 degrees, or between about 25 degrees and about 40 degrees, or between about 20 degrees and 50 degrees, or between about 20 degrees and about 40 degrees, or between about 20 degrees and about 30 degrees.

It is to be further appreciated that the depiction of surgical clip feeder 1200 as containing or having contained six arcuate surgical clips 1210a-f is for purposes of illustration only, as more or less than six arcuate surgical clips may be present in other various embodiments. Longitudinal space within end effector 1100, for example, may dictate the actual number of arcuate surgical clips that may be present. In illustrative embodiments, surgical clip feeder 1200 may contain or be configured to contain between two and ten arcuate surgical clips, or between three and eight arcuate surgical clips, or between four and six arcuate surgical clips. In still other embodiments, surgical clip feeder 1200 may contain or be configured to contain more than ten arcuate surgical clips, without departing from the scope of the disclosure.

Surgical clip feeder 1200 is configured for advancing arcuate surgical clips 1210a-f distally. As depicted in FIG. 12, for example, surgical clip feeder 1200 is distally biased with feed spring 1211, which is engaged with clip shoe 1212. Clip shoe 1212 is configured to transfer a longitudinal load from feed spring 1211 to arcuate surgical clips 1210a-f in order to promote distal translation thereof. Alternative biasing mechanisms, such as those incorporating electrical, mechanical, electromechanical, hydraulic, pneumatic, or magnetic biasing principles, for example, may be used in place of feed spring 1211. Moreover, other techniques for applying a longitudinal load to clip shoe 1212 also reside within the scope of the present disclosure. In some embodiments, for example, feed spring 1211 may be replaced with a push rod or like structure that may be selectively actuated directly from a drive housing or via a geared assembly or the like. In embodiments with a geared assembly, for example, the push rod may be operatively coupled to a cable-driven worm gear positioned adjacent surgical clip feeder 1200, and associated drive cable(s) that move the worm gear may extend thereto from a drive housing and potentially through a wrist.

In some embodiments, distal portions 1206 of jaw members 1105a and 1105b may exhibit a curved profile (arcuate shape profile) matching or similar to that of arcuate surgical clips 1210a-f. Jaw members 1105a and 1105b may include cam tracks 1220, which are depicted in FIG. 12 as lobes extending from jaw members 1105a and 1105b that are along or proximal to distal portions 1206. Cam tracks 1220 may interact with a camming mechanism (not shown in FIG. 12) to promote closure of jaw members 1105a and 1105b during crimping. Although depicted as lobe-shaped, cam tracks 1220 may alternatively comprise other types of camming configurations known in the art without departing from the scope of the present disclosure. Alternative mechanisms for urging jaw members 1105a and 1105b toward one another also reside within the scope of the present disclosure. Upon actuating the camming mechanism, proximal portions 1230 of jaw members 1105a and 1105b flex inwardly as jaw members 1105a and 1105b close upon each other to crimp an arcuate surgical clip interposed therebetween.

Jaw members 1105a and 1105b each may include groove 1240 (one visible in FIG. 12), which generally follows the curvature of jaw members 1105a and 1105b. Grooves 1240 may also match or be similar to the curvature of arcuate surgical clips 1210a-f and are sized to receive the legs of arcuate surgical clips 1210a-f during distal advancement thereof, thereby aiding in maintaining arcuate surgical clips 1210a-f in individual interposition between jaw members 1105a and 1105b. In other embodiments, grooves 1240 may be omitted, with jaw members 1105a and 1105b instead applying a sufficient lateral load on an incoming arcuate surgical clip to facilitate retention until crimping.

End effector 1100 further includes feedbar 1250, which is configured for longitudinal movement. Feedbar 1250 interposes and is configured to slidably translate between surgical clip feeder 1200 and the inner surface of upper housing 1101a (FIG. 11). Alternately, feedbar 1250 may slidably translate between the inner surface of upper housing 1101a and the body of a magazine containing or having contained arcuate surgical clips 1210a-f. Feedbar 1250 may be actuated via an input from a drive housing (not shown) and associated components thereof, as generally discussed above, to advance arcuate surgical clips 1210a-f individually into interposition between jaw members 1105a and 1105b.

In some embodiments, feedbar 1250 may be flexible and configured to bend downward to engage the distal-most arcuate surgical clip positioned within channel 1450, which is defined between jaw members 1105a and 1105b. Specifically, feedbar 1250 may engage the inner contour of tapered section 1102 (FIG. 11) and correspondingly flex into engagement with the crown of the distal-most arcuate surgical clip. Once distal end 1260 of feedbar 1250 engages the crown of the distal-most surgical clip, further distal advancement of feedbar 1250 urges the distal-most arcuate surgical clip (e.g., arcuate surgical clip 1210a) into interposition between jaw members 1105a and 1105b within grooves 1240. This configuration is shown in the exposed, partial top view of FIG. 13.

In some embodiments, distal end 1260 of feedbar 1250 may include a complementary profile configured to engage the crown of the distal-most surgical clip (e.g., arcuate surgical clip 1210a) adjacent to tapered section 1102 (FIG. 11). Proximal to tapered section 1102, in contrast, distal end 1260 is unable to engage the remaining arcuate surgical clips (e.g., arcuate surgical clips 1210b-f) and instead slidably translates relative to (over) the crowns of the remaining arcuate surgical clips or the body of a cartridge containing the remaining arcuate surgical clips. However, upon distal advancement of the remaining arcuate surgical clips into a position adjacent to tapered section 1102, as described hereinafter in reference to FIGS. 14 and 15, feedbar 1250 may promote further individual distal advancement of these surgical clips as well.

Figure 14:
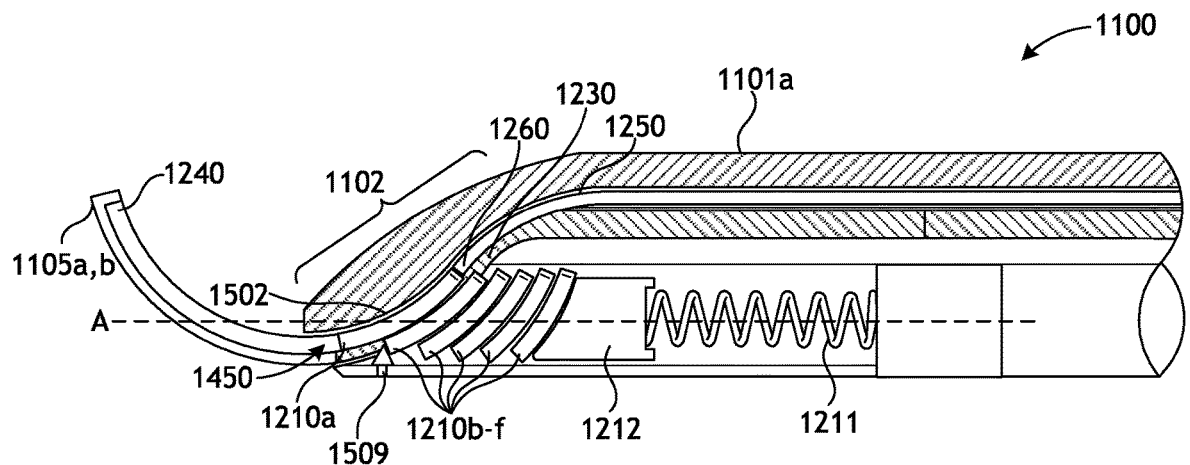
FIGS. 14 and 15 are corresponding cross-sectional side views of the end effector of FIGS. 11-13 at various operational stages.
Figure 15:
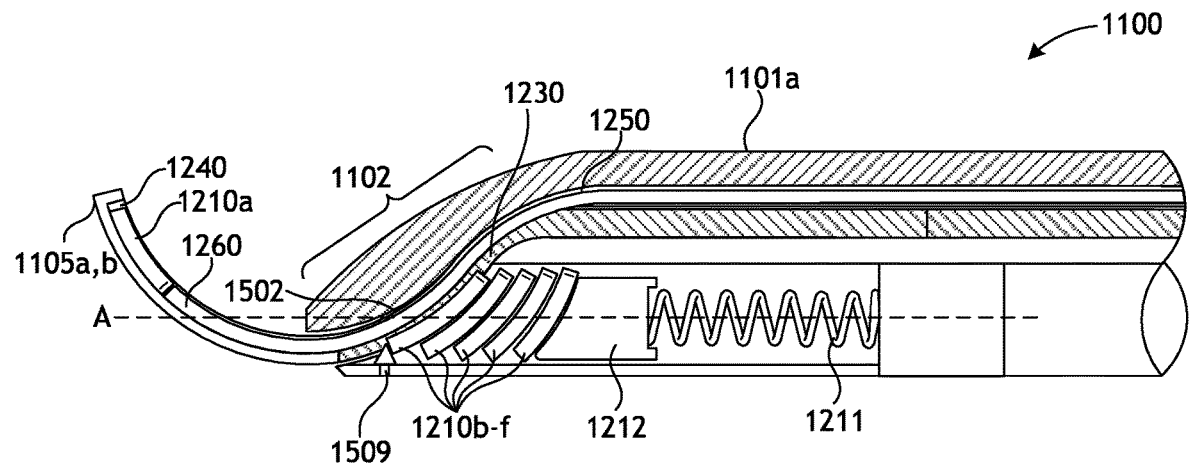

FIGS. 14 and 15 are cross-sectional side views of end effector 1100 at various operational stages thereof, in which additional details concerning distal advancement of arcuate surgical clips 1210a-f are provided. As shown, arcuate surgical clips 1210a-f are nested together, with feed spring 1211 and clip shoe 1212 supplying a longitudinal biasing force thereto. According to some embodiments, the longitudinal biasing force urges arcuate surgical clips 1210a-f distally until the distal-most arcuate surgical clip (e.g., arcuate surgical clip 1210a) engages inner surface 1502 of upper housing 1101a within tapered section 1102, thereby precluding further distal advancement along longitudinal axis A. In some embodiments and as illustrated, inner surface 1502 may be curved or otherwise exhibit a matching arcuate profile similar to that of arcuate surgical clips 1210a-f. In other embodiments, however, inner surface 1502 may exhibit different shapes or profiles that similarly preclude further distal advancement of arcuate surgical clips 1210a-f along longitudinal axis A.

Optionally, spring-loaded stop 1509, which may be opened and closed by rotation or compression, may be provided adjacent to channel 1450 to prevent autonomous advancement of a distal-most arcuate surgical clip into engagement with inner surface 1502 until a desired time. As shown in FIGS. 14 and 15, spring-loaded stop 1509 engages the tips of the legs (tail) of penultimate arcuate surgical clip 1210b to prevent its further distal advancement into channel 1450. Once further distal advancement of penultimate arcuate surgical clip 1210b into engagement with inner surface 1502 is desired, the spring force of spring-loaded stop 1509 may be overcome with an additional biasing force supplied to clip shoe 1212 and/or a force applied to the crown of penultimate arcuate surgical clip 1210b from feedbar 1250, thereby actuating spring-loaded stop 1509 and allowing further distal advancement to take place. In some or other embodiments, a retention mechanism (not shown) may engage the crown of penultimate arcuate surgical clip 1510b to preclude its further distal advancement until a desired time.

Engagement of the distal-most arcuate surgical clip (e.g., arcuate surgical clip 1210a) with inner surface 1502 places the distal-most surgical clip within channel 1450, which is defined between jaw members 1105a and 1105b adjacent to inner surface 1502. Once engaged with inner surface 1502, the tail (i.e., legs) of arcuate surgical clip 1210a may be positioned to enter grooves 1240 of jaw members 1105a and 1105b upon further distal advancement through channel 1450, as discussed hereinafter.

Feedbar 1250 translates longitudinally during operation of end effector 1100 to affect distal advancement of arcuate surgical clips 1210a-f. In some embodiments, feedbar 1250 may be configured to engage and follow the contour of inner surface 1502 and thereby flex downward into channel 1450 (FIG. 12). Within channel 1450, distal end 1260 of feedbar 1250 may engage the crown of the distal-most arcuate surgical clip (e.g., arcuate surgical clip 1210a), which is abutted against inner surface 1502, as shown in FIG. 14. Further distal advancement of feedbar 1250 forces the legs of arcuate surgical clip 1210a into grooves 1240, such that arcuate surgical clip 1210a becomes interposed between jaw members 1105a and 1105b, as shown in FIG. 15. Feedbar 1250 may also include one or more prongs (not shown) for engaging the crown of penultimate arcuate surgical clip 1210b, such as to apply an additional force for feeding penultimate arcuate surgical clip 1210b into channel 1450 and/or for overcoming the spring force of spring-loaded stop 1509.

Figure 16A:
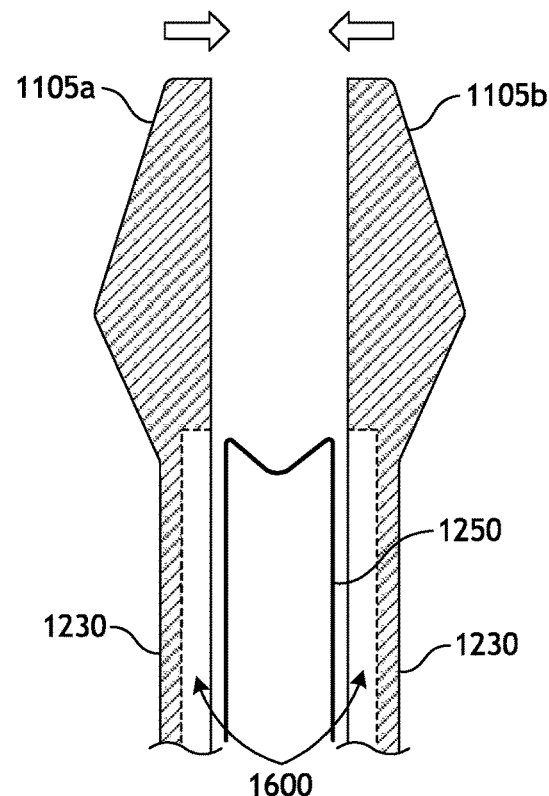
FIGS. 16A and 16B are top cross-sectional views of an end effector having jaw members with a lateral recess.
Figure 16B:
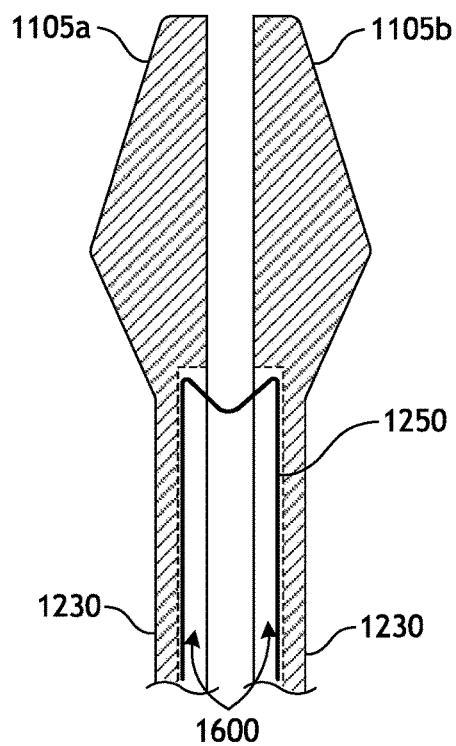

Once arcuate surgical clip 1210a has been positioned between jaw members 1105a and 1105b, feedbar 1250 may then be withdrawn proximally so that crimping of arcuate surgical clip 1210a may take place. In particular, feedbar 1250 may be withdrawn a sufficient proximal distance so that cam-induced closure or similar closure of jaw members 1105a and 1105b may take place. According to some embodiments and as shown in FIGS. 16A and 16B in top cross-sectional view, jaw members 1105a and 1105b may contain lateral recesses 1600 (pockets), which are sized to accommodate feedbar 1250 during closure of jaw members 1105a and 1105b as proximal portions 1230 flex toward one another. Provided that feedbar 1250 continues to occlude channel 1450, dispensation of penultimate arcuate surgical clip 1210b into channel 1450 is precluded, thereby preventing unwanted crimping of penultimate arcuate surgical clip 1210b during closure of jaw members 1105a and 1105b to crimp distal-most arcuate surgical clip 1210a. Further proximal withdrawal of feedbar 1250 in such embodiments leaves channel 1450 open to receive penultimate arcuate surgical clip 1210b for subsequent deployment. As discussed above, distal advancement of penultimate arcuate surgical clip 1210b may be delayed, in some embodiments, by spring-loaded stop 1509.

Once channel 1450 clears following proximal withdrawal of feedbar 1250, the longitudinal biasing force advances arcuate surgical clips 1210b-f distally until a penultimate arcuate surgical clip (e.g., arcuate surgical clip 1210b) engages inner surface 1502 and becomes positioned in channel 1450, optionally after actuating spring-loaded stop 1509. At this juncture, arcuate surgical clip 1210b may then be advanced by feedbar 1250 into interposition between jaw members 1105a and 1105b and crimped in a manner similar to that described above for arcuate surgical clip 1210a. Remaining arcuate surgical clips 1210c-f may be advanced and crimped in a similar manner.

End effector 1100 may be loaded with arcuate surgical clips 1210a-f or another suitable number of arcuate surgical clips during or after assembly, according to various embodiments. In some embodiments, arcuate surgical clips 1210a-f or another suitable number of arcuate surgical clips may be added to end effector 1100 in a cartridge, magazine, or similar structure. The terms "cartridge" and "magazine" are used synonymously herein to denote a structure in which multiple arcuate surgical clips can be housed for simultaneous loading within end effector 1100. Various cartridge or magazine configurations may be suitable for use in conjunction with end effector 1100 and other similar end effectors of the present disclosure.

Figure 17A:
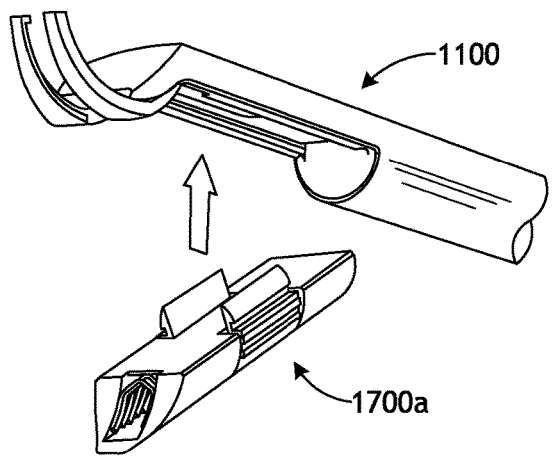
FIGS. 17A-17F are isometric views of cartridges loaded with arcuate surgical clips and their various coupling motifs to an end effector.
Figure 17B:
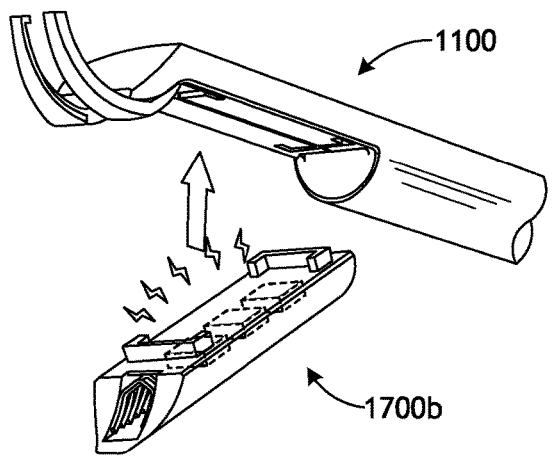
Figure 17C:
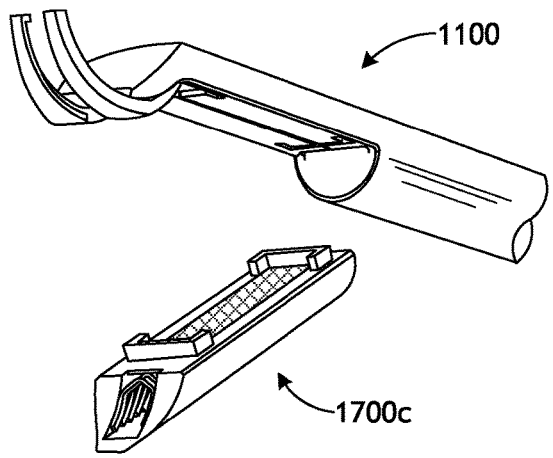
Figure 17D:
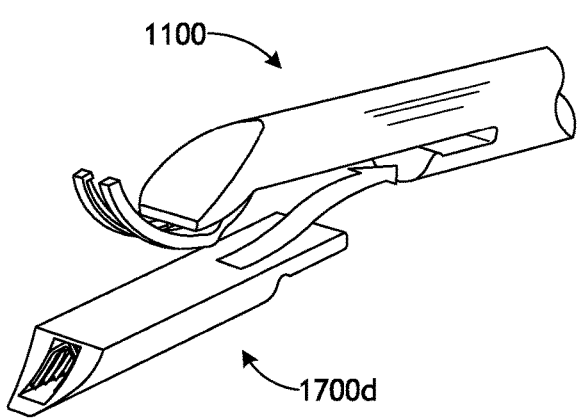
Figure 17E:
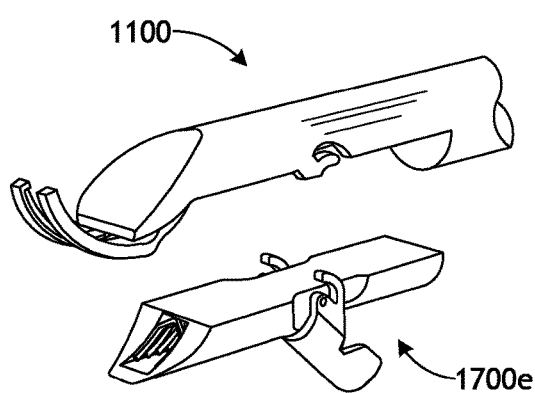
Figure 17F:
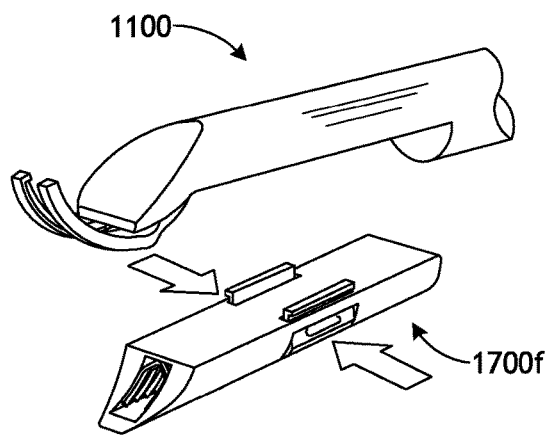

FIGS. 17A-17F show suitable configurations of cartridges 1700a-f, respectively, containing arcuate surgical clips that may be removably connected to an end effector through a complementary coupling motif. In illustrative embodiments, coupling to end effector 1100 may take place mechanically, as shown in FIGS. 17A and 17D-17F, magnetically, as shown in FIG. 17B, and/or adhesively, as shown in FIG. 17C. Mechanical coupling motifs may include, for example, snap tab connections (FIG. 17A), snap fit connections (FIG. 17D), cam-lever connections (FIG. 17E), and push-button tab connections (FIG. 17F). The principles by which cartridges 1700a-f are removably connected to end effector 1100 will be familiar to one having ordinary skill in the art and are not described herein in any further detail.

In illustrative embodiments, feed spring 1211 and clip shoe 1212 may be contained within the interior of cartridges 1700a-f or related cartridges that may be removably coupled to end effector 1100 based upon similar principles. Loading of arcuate surgical clips 1210a-f or another number of arcuate surgical clips within cartridges 1700a-f may compress feed spring 1211, which may then decompress and exert a longitudinal biasing force once the cartridge has been coupled to end effector 1100, as discussed in more detail above. In use, cartridges 1700a-f or similar cartridges may be dispensed to completion, according to some embodiments, or, in other various embodiments, multiple cartridges 1700a-f containing different sizes and/or types or arcuate surgical clips 1210a-f may be employed during a surgical procedure. In still other embodiments, multiple cartridges 1700a-f or similar cartridges containing the same size and/or type of arcuate surgical clips 1210a-f may be employed during a surgical procedure, for example, if a single cartridge 1700a-f contains an insufficient number of arcuate surgical clips 1210a-f to complete a desired surgical task.

Embodiments disclosed herein include:

A. End effectors for a surgical clip applier. The end effectors comprise: a housing; and first and second arcuate jaw members protruding distally from the housing, each arcuate jaw member having a curved profile and being shaped to receive an arcuate surgical clip having a complementary curved profile therebetween.

B. Surgical tools. The surgical tools comprise: a drive housing; an elongate shaft extending from the drive housing; and an end effector operatively coupled to a distal end of the elongate shaft, the end effector comprising: a housing; and first and second arcuate jaw members protruding distally from the housing, each arcuate jaw member having a curved profile and being shaped to receive an arcuate surgical clip having a complementary curved profile therebetween.

C. Methods for using a surgical tool. The methods comprise: positioning a surgical tool having an end effector adjacent to a surgical site, the end effector comprising: a housing; first and second arcuate jaw members protruding distally from the housing and having a channel defined therebetween; a surgical clip feeder positionable within the housing in communication with the channel and containing or configured to contain a plurality of arcuate surgical clips in a nested configuration; and a feedbar movable relative to the surgical clip feeder; engaging the feedbar on a distal-most arcuate surgical clip of the plurality of arcuate surgical clips, the distal-most arcuate surgical clip being arranged within the channel; advancing the distal-most arcuate surgical clip through the channel with the feedbar and into interposition between the first and second arcuate jaw members; and at least partially collapsing the first and second arcuate jaw members to crimp the distal-most arcuate surgical clip.

Each of embodiments A, B, and C may have one or more of the following additional elements in any combination.

Element 1: wherein the housing has a tapered section at a distal end thereof, the first and second arcuate jaw members protruding distally from the tapered section.

Element 2: wherein the end effector further comprises: a surgical clip feeder positionable within the housing and configured to house a plurality of arcuate surgical clips in a nested configuration; a channel defined between the first and second arcuate jaw members for receiving a distal-most arcuate surgical clip from the surgical clip feeder; and a feedbar movable relative to the surgical clip feeder and engageable with the distal-most arcuate surgical clip; wherein the feedbar is adapted for advancing the distal-most arcuate surgical clip from the channel into interposition between the first and second arcuate jaw members.

Element 3: wherein the surgical clip feeder is arranged within a cartridge removably coupled to the housing.

Element 4: wherein the feedbar comprises a flexible material that allows the feedbar to follow an inner surface of the tapered section during movement of the feedbar.

Element 5: wherein the surgical clip feeder is distally biased.

Element 6: wherein the end effector further comprises a camming mechanism movable to collapse the first and second arcuate jaw members.

Element 7: wherein the end effector further comprises a groove defined on an inner surface of each arcuate jaw member and exhibiting the curved profile.

Element 8: wherein the surgical tool further comprises an articulable wrist that interposes and couples the end effector to the distal end of the elongate shaft.

Element 9: wherein the method further comprises proximally withdrawing the feedbar; and distally advancing a penultimate arcuate surgical clip of the plurality of arcuate surgical clips into the channel with the surgical clip feeder.

Element 10: wherein the method further comprises applying a distal biasing force with the surgical clip feeder to advance the penultimate arcuate surgical clip into the channel.

Element 11: wherein the method further comprises operably connecting a cartridge to the end effector, the cartridge containing the surgical clip feeder.

By way of non-limiting example, exemplary combinations applicable to A, B, and C include:

The end effector of A in combination with elements 1 and 2; 1 and 3; 1 and 4; 1 and 5; 1 and 6; 1 and 7; 2 and 3; 2 and 4; 2 and 5; 2 and 6; 2 and 7; 3 and 4; 3 and 5; 3 and 6; 3 and 7; 4 and 5; 4 and 6; 4 and 7; 5 and 6; 5 and 7; 6 and 7; 1, 2 and 3; 1, 2 and 4; 1, 2 and 5; 1, 2 and 6; 1, 2 and 7; 1-4; and 1, 2, 4 and 5.

The surgical tool of B in combination with elements 1 and 2; 1 and 3; 1 and 4; 1 and 5; 1 and 6; 1 and 7; 2 and 3; 2 and 4; 2 and 5; 2 and 6; 2 and 7; 3 and 4; 3 and 5; 3 and 6; 3 and 7; 4 and 5; 4 and 6; 4 and 7; 5 and 6; 5 and 7; 6 and 7; 1, 2 and 3; 1, 2 and 4; 1, 2 and 5; 1, 2 and 6; 1, 2 and 7; 1-4; 1, 2, 4 and 5, any of which may be in further combination with element 8. The surgical tool of B in combination with elements 1 and 8; 2 and 8; 3 and 8; 4 and 8; 5 and 8; 6 and 8; and 7 and 8.

The method of C in combination with elements 1 and 4; 1 and 5; 1 and 6; 4 and 5; 4 and 6; 4 and 7; 5 and 6; 5 and 7; 6 and 7; 9 and 10; 9 and 11; 10 and 11; 9-11; 1 and 9; 4 and 9; 5 and 9; 6 and 9; 7 and 9; 1, 9 and 10; 4, 9 and 10; 5, 9 and 10; 6, 9 and 10; 7, 9 and 10, any of which may be in further combination with element 8.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
   positioning a surgical tool with an end effector adjacent a surgical site, the end effector comprising:
   a housing having a tapered section that defines an inner surface;
   first and second arcuate jaw members protruding distally from the housing and defining a channel therebetween, each arcuate jaw member exhibiting a curved profile shaped to receive an arcuate surgical clip; and
   a feedbar movable within the housing and disengaged from the arcuate surgical clip;
   urging the arcuate surgical clip against the inner surface;
   advancing the feedbar within the housing to engage and follow the inner surface and thereby flexing the feedbar downward and into engagement with the arcuate surgical clip;
   advancing the arcuate surgical clip with the feedbar into interposition between the first and second arcuate jaw members; and
   collapsing the first and second arcuate jaw members to crimp the arcuate surgical clip.

2. The method of claim 1, wherein the arcuate surgical clip comprises a distal-most arcuate surgical clip of a plurality of arcuate surgical clips positioned within a surgical clip feeder arranged within the housing, and wherein urging the arcuate surgical clip against the inner surface comprises:
   receiving the distal-most arcuate surgical clip from the surgical clip feeder into the channel defined between the first and second arcuate jaw members; and
   advancing the distal-most arcuate surgical clip with the feedbar from the channel into interposition between the first and second arcuate jaw members.

3. The method of claim 2, wherein the surgical clip feeder is arranged within a removable cartridge, and wherein positioning the surgical tool adjacent the surgical site is preceded by removably coupling the removable cartridge to the housing.

4. The method of claim 2, further comprising:
   proximally withdrawing the feedbar;
   urging a penultimate arcuate surgical clip of the plurality of arcuate surgical clips against the inner surface;
   advancing the feedbar within the housing thereby flexing the feedbar downward and into engagement with the penultimate arcuate surgical clip;
   advancing the penultimate arcuate surgical clip with the feedbar into interposition between the first and second arcuate jaw members; and
   collapsing the first and second arcuate jaw members to crimp the penultimate arcuate surgical clip.

5. The method of claim 4, wherein urging the penultimate arcuate surgical clip against the inner surface comprises applying a distal biasing force against the penultimate arcuate surgical clip with the surgical clip feeder.

6. The method of claim 4, wherein urging the penultimate arcuate surgical clip against the inner surface comprises:
   engaging the penultimate arcuate surgical clip against a spring-loaded stop included in the surgical clip feeder and thereby preventing the penultimate arcuate surgical clip from engaging the inner surface; and
   overcoming spring force of the spring-loaded stop by applying a distal biasing force against the penultimate arcuate surgical clip with the surgical clip feeder.

7. The method of claim 4, wherein proximally withdrawing the feedbar is preceded by preventing the penultimate arcuate surgical clip from engaging the inner surface with the feedbar.

8. The method of claim 1, wherein advancing the arcuate surgical clip into interposition between the first and second arcuate jaw members comprises advancing the arcuate surgical clip with the feedbar into a groove defined on an inner surface of each arcuate jaw member, the groove exhibiting the curved profile.

9. The method of claim 1, wherein the inner surface of the tapered section is arcuate and a curvature of the inner surface matches a curved profile of the arcuate surgical clip, and wherein urging the arcuate surgical clip against the inner surface comprises:
   applying a longitudinal biasing force against the arcuate surgical clip; and
   preventing further distal advancement along a longitudinal axis of the end effector by engaging the arcuate surgical clip against the inner surface.

10. The method of claim 1, wherein collapsing the first and second arcuate jaw members comprises:
    proximally withdrawing the feedbar;
    urging the first and second arcuate jaw members toward one another; and
    receiving the feedbar within a lateral recess defined in each arcuate jaw member as the first and second arcuate jaw members move toward one another.

11. The method of claim 1, wherein urging the arcuate surgical clip against the inner surface occurs prior to advancing the feedbar.

12. A method, comprising:
    positioning a surgical tool having an end effector adjacent a surgical site, the end effector comprising:
    a housing having a tapered section that defines an inner surface;
    first and second arcuate jaw members protruding distally from the housing and having a channel defined therebetween;
    a surgical clip feeder positionable within the housing and containing a plurality of arcuate surgical clips; and
    a feedbar movable between the inner surface and the surgical clip feeder;

urging a distal-most arcuate surgical clip of the plurality of arcuate surgical clips against the inner surface and within the channel;

advancing the feedbar within the housing to engage and follow the inner surface and thereby flexing the feedbar downward and into engagement with the distal-most arcuate surgical clip;

advancing the distal-most arcuate surgical clip through the channel with the feedbar and into interposition between the first and second arcuate jaw members; and collapsing the first and second arcuate jaw members to crimp the distal-most arcuate surgical clip.

13. The method of claim 12, further comprising:
proximally withdrawing the feedbar; and
distally advancing a penultimate arcuate surgical clip of the plurality of arcuate surgical clips against the inner surface and into the channel with the surgical clip feeder.

14. The method of claim 13, wherein proximally withdrawing the feedbar is preceded by preventing the penultimate arcuate surgical clip from engaging the inner surface with the feedbar.

15. The method of claim 14, further comprising applying a distal biasing force with the surgical clip feeder to advance the penultimate arcuate surgical clip into the channel.

16. The method of claim 12, wherein the inner surface of the tapered section is arcuate and a curvature of the inner surface matches a curved profile of the arcuate surgical clip, and wherein urging the distal-most arcuate surgical clip against the inner surface comprises:
applying a longitudinal biasing force against the distal-most arcuate surgical clip; and
preventing further distal advancement along a longitudinal axis of the end effector by engaging the distal-most arcuate surgical clip against the inner surface.

17. The method of claim 12, wherein urging the distal-most arcuate surgical clip against the inner surface comprises:
engaging the distal-most arcuate surgical clip against a spring-loaded stop included in the surgical clip feeder and thereby preventing the distal-most arcuate surgical clip from engaging the inner surface; and
overcoming spring force of the spring-loaded stop by applying a distal biasing force against the distal-most arcuate surgical clip with the surgical clip feeder.

18. The method of claim 12, wherein collapsing the first and second arcuate jaw members comprises:
proximally withdrawing the feedbar;
urging the first and second arcuate jaw members toward one another; and
receiving the feedbar within a lateral recess defined in each arcuate jaw member as the first and second arcuate jaw members move toward one another.

19. The method of claim 12, wherein the surgical clip feeder is arranged within a removable cartridge, and wherein positioning the surgical tool adjacent the surgical site is preceded by removably coupling the removable cartridge to the housing.

20. The method of claim 12, wherein the distal-most arcuate surgical clip of the plurality of arcuate surgical clips is urged against the inner surface and within the channel via a feed spring and a clip shoe of the surgical clip feeder.

* * * * *